(12) United States Patent
Berry et al.

(10) Patent No.: US 11,965,828 B2
(45) Date of Patent: Apr. 23, 2024

(54) VARIABLE LIGHT DIFFUSER FOR PLANT LEAF GAS EXCHANGE MEASUREMENTS

(71) Applicant: Chapman University, Orange, CA (US)

(72) Inventors: Z. Carter Berry, Winston-Salem, NC (US); Gregory R. Goldsmith, Orange, CA (US); Fernando Silva, Santa Ana, CA (US)

(73) Assignee: Chapman University, Orange, CA (US)

( * ) Notice: Subject to any disclaimer, the term of this patent is extended or adjusted under 35 U.S.C. 154(b) by 383 days.

(21) Appl. No.: 17/399,861

(22) Filed: Aug. 11, 2021

(65) Prior Publication Data

US 2022/0050052 A1  Feb. 17, 2022

Related U.S. Application Data

(60) Provisional application No. 63/064,324, filed on Aug. 11, 2020.

(51) Int. Cl.
  *G01N 21/3504* (2014.01)
  *G01N 21/84* (2006.01)
  *G01N 33/00* (2006.01)

(52) U.S. Cl.
  CPC ......... *G01N 21/3504* (2013.01); *G01N 21/84* (2013.01); *G01N 33/0098* (2013.01); *G01N 2021/8466* (2013.01); *G01N 2201/0216* (2013.01); *G01N 2201/062* (2013.01)

(58) Field of Classification Search
  None
  See application file for complete search history.

(56) References Cited

U.S. PATENT DOCUMENTS

| | | | | | |
|---|---|---|---|---|---|
| 4,487,504 | A | * | 12/1984 | Goldsmith | G01N 21/474 356/323 |
| 4,932,779 | A | * | 6/1990 | Keane | G01J 3/08 356/323 |
| 9,528,932 | B2 | * | 12/2016 | Moggridge | G01N 21/4738 |
| 2015/0377770 | A1 | * | 12/2015 | Eura | G01J 3/0291 356/402 |

FOREIGN PATENT DOCUMENTS

JP      2002048713 A  *  2/2002

* cited by examiner

*Primary Examiner* — Edwin C Gunberg
(74) *Attorney, Agent, or Firm* — K&L Gates LLP; Louis C. Cullman; Michelle Glasky Bergman

(57) ABSTRACT

Disclosed herein are light diffuser devices comprising a sphere having at least two openings, a track, a light source, a cart, and one or more plates, and their methods of use. Also, disclosed here are light diffuser systems comprising a light diffuser device and a portable infrared gas analyzer.

20 Claims, 24 Drawing Sheets

VARIABLE LIGHT DIFFUSER FOR PLANT LEAF GAS EXCHANGE MEASUREMENTS

CROSS REFERENCE TO RELATED APPLICATION

This application claims the benefit of priority to U.S. Provisional Patent Application No. 63/064,324, filed Aug. 11, 2020, the entire disclosure which is incorporated herein by reference.

FIELD

Described herein are systems and devices that can control distributions of angles of light and the methods of using the systems and devices. In particular, the devices can be light diffuser spheres or integrating spheres.

BACKGROUND

Experimental measurements of leaf gas exchange are a cornerstone of plant physiology in both basic and applied settings. Measurements made using infrared gas analyzers often utilize artificial light sources composed of a mix of different colored lights that allow for the precise control of both the quantity and spectral distribution of light. In addition to the quantity and spectral quality of light, the angle of incidence for light arriving at the surface of the leaf should also be considered. The plant physiology community implicitly assumes that the light emanating from artificial light sources is direct, insomuch as the angle of incidence is perpendicular to the leaf surface. This is consistent with direct light emanating from the sun in the absence of significant aerosols.

There is growing recognition that plants are frequently subject to light that is not direct, but rather a mix of direct and diffuse light. Diffuse light can have a significant effect on leaf gas exchange, with implications for ecosystem level carbon and water fluxes. Thus, there is a need to understand the angular distribution of the light emanating from artificial light sources, as well as to develop tools that allow for the precise control of the distribution of the angles of light reaching the surface of a leaf being assessed for its gas exchange properties. At present, commercially available systems provide light sources (commonly composed of LEDs) of an unknown distribution. Described herein are systems comprising light diffuser devices that effectively control the distribution of the angles of light reaching the leaf surface, creating a range of possible distributions from almost entirely direct light (light from a 90° angle perpendicular to the leaf surface) to almost entirely diffuse light (light from an even distribution drawn from a nearly 0° horizontal angle to a perpendicular 90° angle).

SUMMARY

Described herein are light diffuser spheres or integrating spheres that can control distributions of angles of light reaching a surface. In some embodiments, the surface is a surface of a leaf. The terms, light diffuser sphere(s) and integrating sphere(s), are interchangeable throughout this disclosure. Also, the terms, light diffuser sphere(s) and light diffuser device(s), are interchangeable throughout this disclosure.

In some embodiments, a light diffuser sphere/device comprises a moveable port/opening that allows for the delivery of variable proportions of diffuse light, integrates directly with a portable infrared leaf gas analyzer, and directly utilizes the light source that comes with the leaf gas analyzer. In other embodiments, a light diffuser sphere/device comprises a moveable port/opening that allows for the delivery of variable proportions of diffuse light and integrates directly with a portable infrared leaf gas analyzer. The moveable port/opening can include a light source.

Also, described herein are systems that can control distributions of angles of light. In some embodiments, a system is comprised of a light diffuser device described herein and a gas analyzer. The gas analyzer can be an infrared gas analyzer.

In some embodiments, a light diffuser device comprises a sphere having at least two openings, a track, a light source, a cart, and one or more plates.

BRIEF DESCRIPTION OF DRAWINGS

FIG. 15A depicts light response curves for *Ocotea tonduzii*. FIG. 15B depicts light response curves for *Meliosma vernicosa*. FIG. 15C depicts light response curves for *Conostegia rufescens*. FIG. 15D depicts light response curves for *Heliocarpus americana*. FIG. 15E depicts light response curves for *Ocotea meziana*. FIG. 15F depicts light response curves for *Elaeagia auriculata*. FIG. 15G depicts light response curves for *Ficus* spp. FIG. 15H depicts light response curves for *Cecropia polyphlebia*. Data were collected using the Li-Cor LI-6800 (Li-Cor Inc. Lincoln, NE, USA) modified with an attached integrating diffuser sphere to create diffuse light conditions. Temperature was held at 22° C., $CO_2$ concentration at 400 ppm, and relative humidity at 70%. Data are means±SE.

FIG. 16A depicts measurements taken from the species when the leaves were dry. FIG. 16B depicts measurements taken from the species when the leaves were wet. Values that are above zero had greater photosynthesis under direct light conditions, and those below zero had greater photosynthesis under diffuse light conditions. Points represent the average of five to seven individuals±SE, with the boxplot representing the distribution of all species.

FIG. 17A depicts the difference in leaf photosynthesis measured with direct and diffuse light as a function of specific leaf area for individuals of different canopy tree species. FIG. 17B depicts the difference in leaf photosynthesis measured with direct and diffuse light as a function of leaf dry matter content for individuals of different canopy tree species. FIG. 17C depicts the difference in leaf photosynthesis measured with direct and diffuse light as a function of leaf thickness for individuals of different canopy tree species. FIG. 17D depicts the difference in leaf photosynthesis measured with direct and diffuse light as a function of light saturation point for individuals of different canopy tree species. The relationship in FIG. 17C was not significant when all species were included, but became significant (p=0.003) when the multi-species grouping of *Ficus* spp. was excluded.

FIG. 18A depicts the relationship between the response to diffuse light and the response to leaf wetting. FIG. 18B depicts the relationship between the response to diffuse light and instantaneous photosynthesis. FIG. 18C depicts the relationship between the response to leaf wetting and instantaneous photosynthesis under dry conditions. There was a significant positive relationship between the response to diffuse light and the response to wetting as depicted by FIG. 18A where p=0.008, and instantaneous light-saturated photosynthesis as depicted by FIG. 18B where p<0.0001. There was also a significant positive relationship between the response to wetting and instantaneous photosynthesis as depicted by FIG. 18C where p=0.0125. Points represent the species level arrange±standard error.

FIG. 19A depicts the difference in photosynthesis measured on dry versus wet leaves as a function of leaf water storage capacity (p=0.05, $r^2$=0.4) for individuals of different canopy tree species. FIG. 19B depicts the difference in photosynthesis measured on dry versus wet leaves as a function of stomatal density on the abaxial surface of leaves (p=0.01, $r^2$=0.15) for individuals of different canopy tree species.

DETAILED DESCRIPTION

Figure 1:
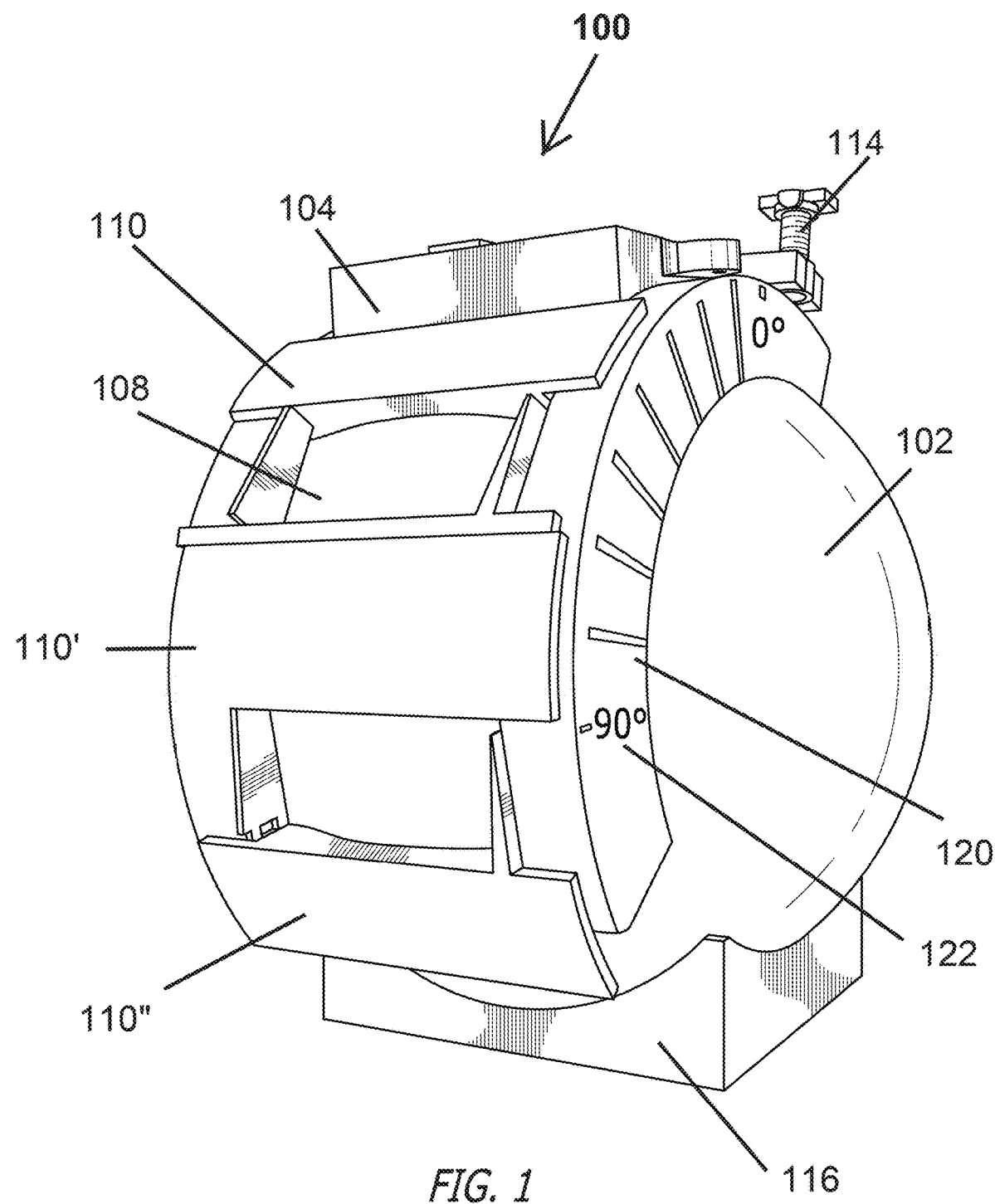
FIG. 1 illustrates a front view of a light diffuser device described herein.

Described herein are integrating spheres that can take direct (collimated) light and turn it into diffuse (angled) light. An integrating sphere is an instrument used to uniformly scatter light, creating a diffuse light environment. Integrating spheres can come in a wide array of sizes and designs depending on the application. The unifying traits of all integrating spheres comprise a hollow sphere, a highly reflective interior coating (to reflect and scatter light), and at least two openings to allow for entrance and exit of light into the sphere. Light rays are sent into the sphere through a first opening and that light is reflected off the inner surface equally to all other points within the sphere. This reflection process continues and results in the light arriving at a second opening to be uniformly scattered, i.e. arriving equally from all angles. Importantly, the quantity of light at the second opening is the same as that of the first opening; however, the original directionality of the light is replaced by light arriving from many angles.

Described herein are light diffuser spheres configured to allow for control of the proportion of direct vs. diffuse light (i.e., different distributions of angles of light). In some embodiments, the light diffuser spheres described herein are configured to allow for control of the proportion of direct vs. diffuse light delivered to a surface of a plant leaf for the purposes of measurement of leaf gas exchange (e.g., photosynthesis and transpiration). The light diffuser spheres described herein are configured to integrate with gas analyzers. In some embodiments, the light diffuser spheres described herein are configured to integrate with traditional portable infrared gas analyzers that measure leaf gas exchange rates. Leaf photosynthesis requires light (solar radiation). Therefore, when measuring leaf gas exchange rates, researchers must control the quantity of light that is arriving at the leaf in order make comparable measurements. Thus, all portable infrared gas analysis equipment that measures photosynthetic processes allows for the control of the precise quantity of light.

Recent research has demonstrated that the angle of light (the proportion of light that is diffuse or direct) also alters leaf gas exchange. Diffuse light occurs whenever it is cloudy or there is particulate matter in the air (e.g., dust or pollution). The current infrared gas analysis equipment on the market is not capable of providing a diffuse light source, and therefore researchers are unable to quantify how diffuse light affects leaf gas exchange. As such, the light diffuser spheres described herein are capable of providing a diffuse light source, therefore allowing researchers to quantify how diffuse light affects leaf gas exchange. As such, the light diffuser spheres described herein are configured to allow researchers to quantify photosynthetic rates along this new axis of variation. The light diffuser spheres described herein are depicted in the accompanying FIGS.

In some embodiments, a light diffuser device comprises a sphere having at least two openings, a cart, a light source, a track, and one or more plates. Light diffuser device 100 is illustrated in FIG. 1 comprising sphere 102 having at least two openings, cart 104, a light source, track 108, and one or more plates 110, 110', 110". The sphere can be hollow. In some embodiments, the sphere can be completely hollow or partially hollow. The track can wrap around a portion of the sphere.

In some embodiments, the sphere can have one opening, two openings, three openings, four openings, or four or more openings. In other embodiments, the openings of the sphere can be any shape or size. In some embodiments, one of the openings of the sphere can be any shape configured to fit any gas analyzer. The gas analyzer can be an infrared gas analyzer. In other embodiments, one of the openings of the sphere can be in the shape of a square with supports that slide directly onto the support plate of a typical leaf gas analyzer chamber. FIG. 1 illustrates an opening which is in the shape of a square base 116 having supports that can slide directly onto the support plate of a leaf gas analyzer. Each infrared gas analyzer can have a slightly different support plate design that requires a slightly different means of connection.

Figure 4:
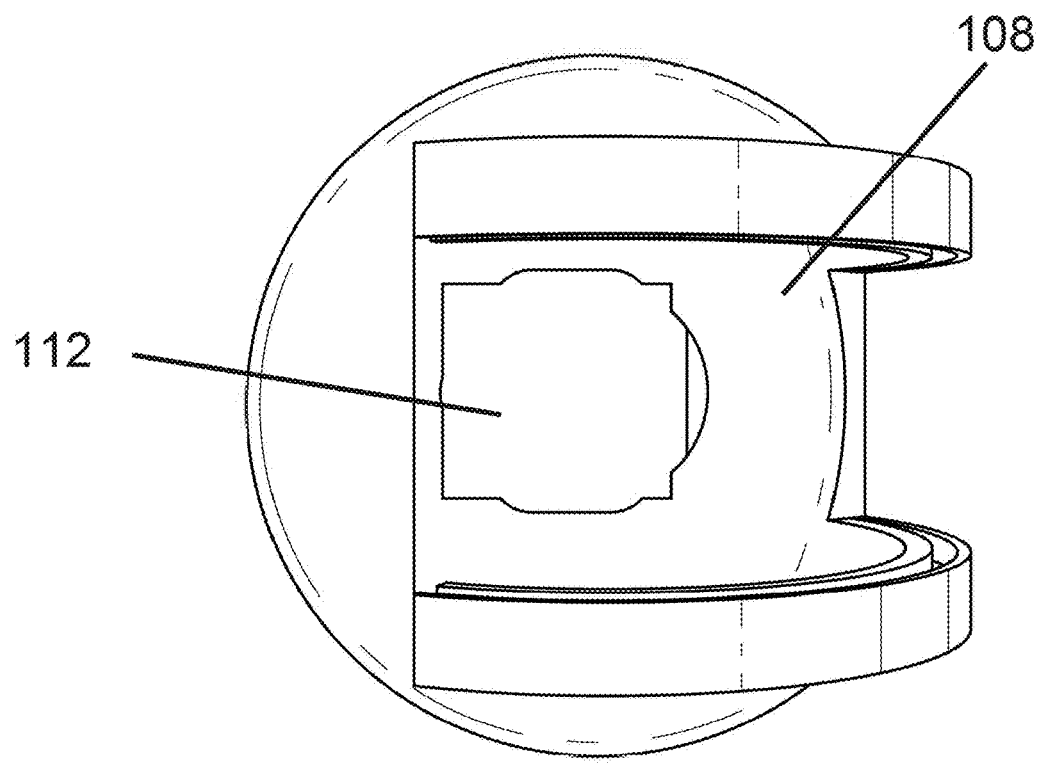
FIG. 4 illustrates a top view of a light diffuser device described herein.
Figure 5:
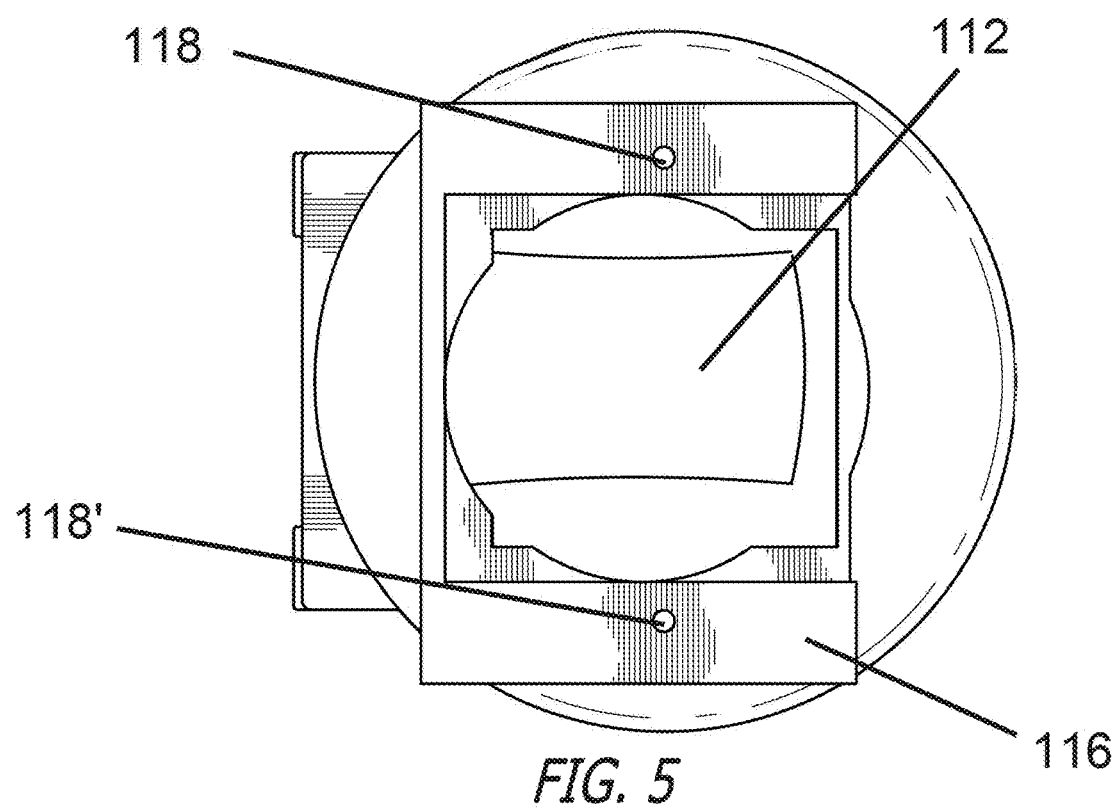
FIG. 5 illustrates a bottom view of a light diffuser device described herein.

In some embodiments, the sphere can be comprised of at least two openings. The openings can be configured to interface with a gas analyzer and/or a light source. In other embodiments, one of the at least two openings can be configured to interface directly with a leaf chamber on a portable infrared leaf gas analyzer, and the other one of the at least two openings can be configured to interface with a cart housing a light source. FIG. 4 illustrates the positioning of track 108 and its orientation relative to opening 112 that is configured to attach to the leaf chamber of the gas analyzer. A top-down view of the diffusing sphere as illustrated in FIG. 4, shows the positioning of track 108 along the right side of the figure and how track 108 is oriented relative to opening 112 that attaches to the leaf chamber of a gas analyzer. In some embodiments, as illustrated by FIG. 5, opening 112 can comprise base 116 having support(s) that can slide onto a support plate of a leaf gas analyzer. In other embodiments, opening 112 can include an adapter component that can be mounted onto a leaf chamber of a gas analyzer. In some embodiments, the gas analyzer is an infrared portable gas analyzer. Opening 112 comprising base 116 having support(s) as illustrated in FIG. 5, can be fitted to the LI-COR Biosciences LI-6800 portable infrared gas analyzer.

Figure 6:
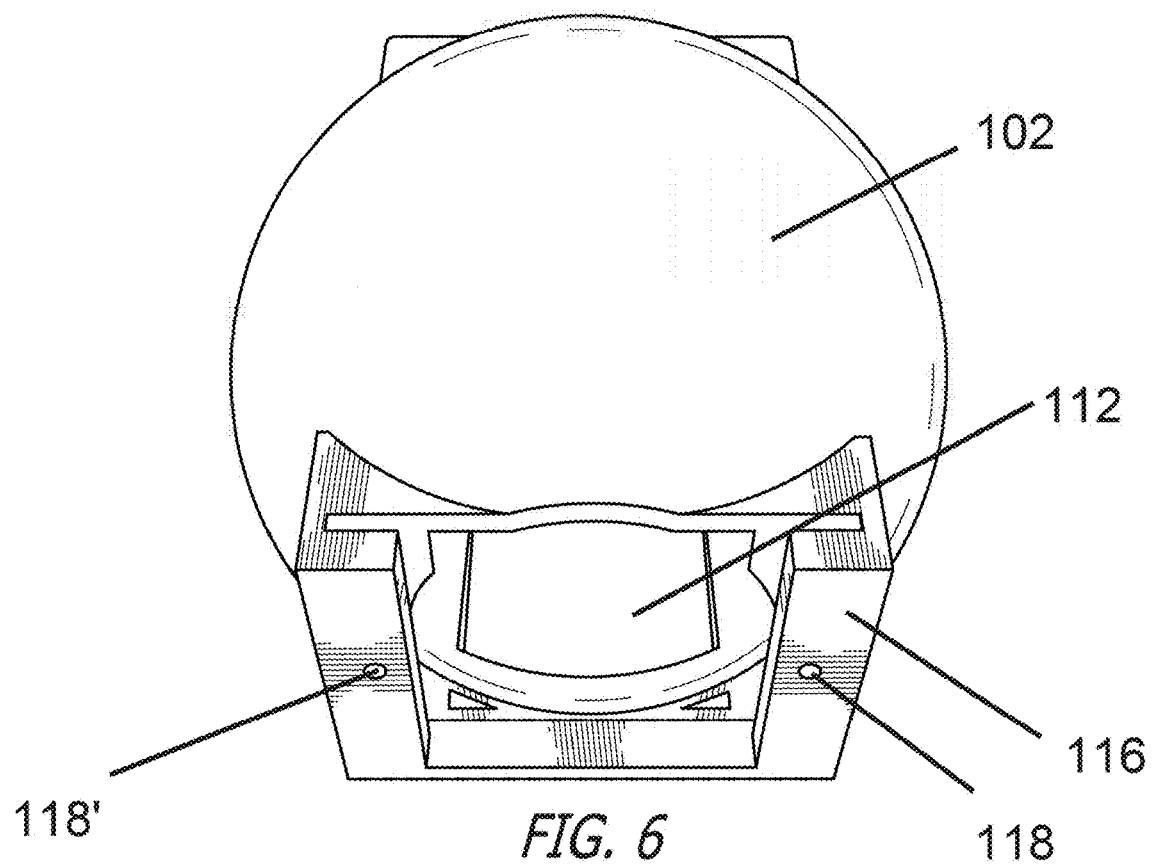
FIG. 6 illustrates a bottom perspective view of a light diffuser device described herein.

FIG. 6 depicts a different angle of FIG. 5 showing opening 112 comprising base 116 having supports and 118, 118. In FIG. 6, the supports can slide onto a leaf chamber of a gas analyzer. The configuration depicted in FIG. 6 can be fitted to a LI-COR Biosciences LI-6800 portable infrared gas analyzer. In some embodiments, screw(s) can be designed to align with the large leaf chamber as illustrated by FIG. 6.

In some embodiments, the base having support(s) can be secured to the sphere via a securing mechanism, such as, but not limited to, fastening and/or adhesion. In other embodiments, the securing mechanism can occur via fastening with a threaded fastener, such as, but not limited to, bolts, screws, studs, and/or a combination thereof. The base can include holes that are configured to attach the sphere to the base via a fastener or securing mechanism. In some embodiments, there can be at least two holes 118, 118' included on base 116 as illustrated in FIGS. 5 and 6. In other embodiments, there can be two or more holes, such as, but not limited to, three holes, four holes, five holes, six holes, seven holes, or eight holes. In some embodiments, the base can have two holes which are secured onto the sphere via screws.

Figure 2:
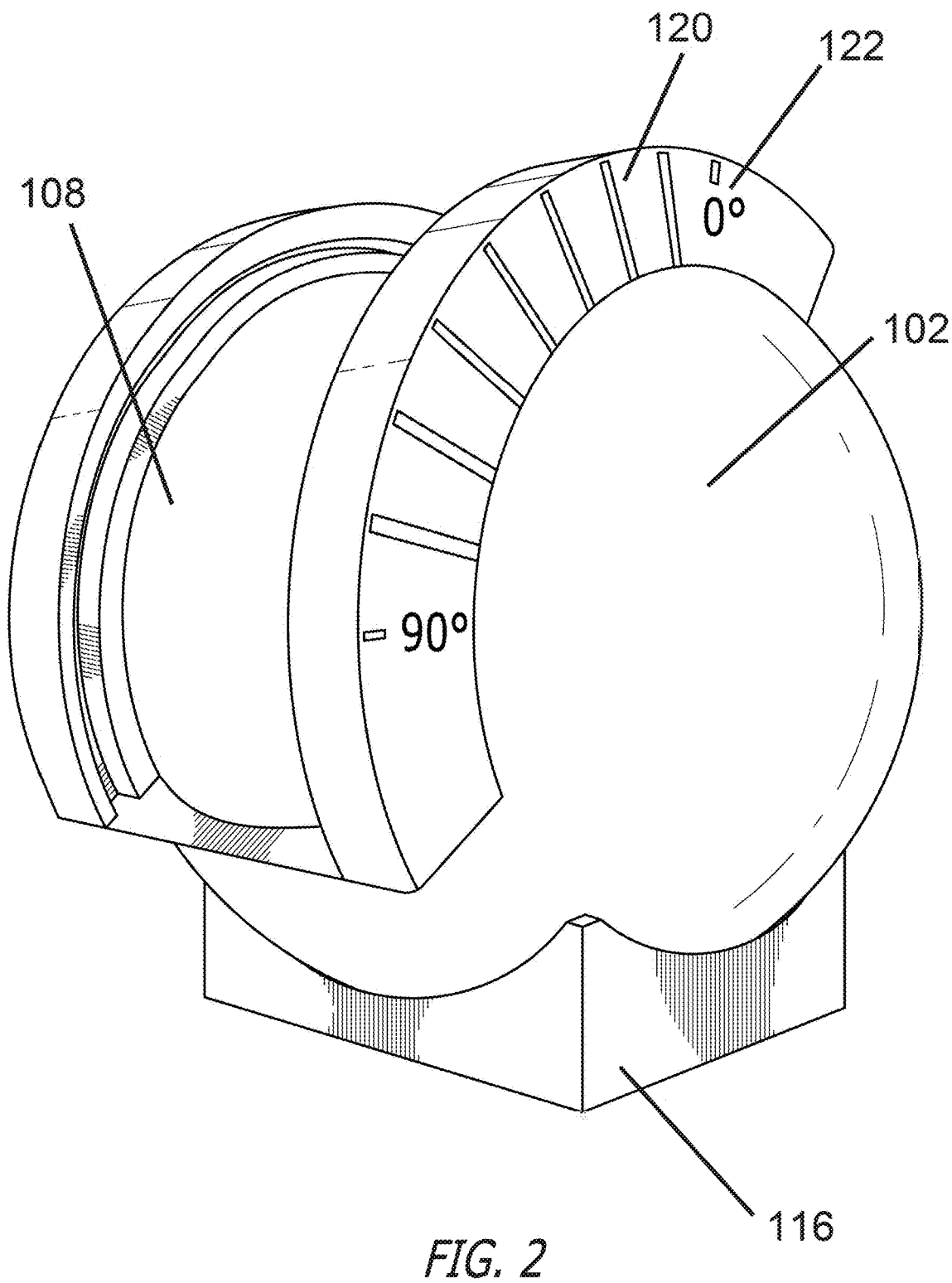
FIG. 2 illustrates another front-angled view of a light diffuser device described herein.

Another opening of the sphere can be for track 108. The track can take any shape or size. In some embodiments, the track is rectangular. In other embodiments, track 108 is rectangular and can run a number of degrees around the side of the sphere as illustrated in FIG. 2. Light diffuser device 100 is depicted in FIG. 2 without cart 104 and plates 110, 110', 110" thereby revealing the notched spacing of track 108 that allows for guides of the components of light diffuser device 100. In other embodiments, track 108 does not include notched spacing. In some embodiments, track 108 can include any means needed to guide components of the light diffuser device.

In some embodiments, the track can run about 10°, about 20°, about 30°, about 40°, about 50°, about 60°, about 70°, about 80°, about 90°, about 100°, about 110°, about 120°, about 130°, about 140°, about 150°, about 160°, about 170°, about 180°, 10°, 20°, 30°, 40°, 50°, 60°, 70°, 80°, 90°, 100°, 110°, 120°, 130°, 140°, 150°, 160°, 170°, 180°, between about 10° and about 90°, between about 10° and about 120°, or between about 90° and about 180° around the side of the sphere. In other embodiments, the track can be rectangular and run 120° around the side of the sphere. In some embodiments, the track can span 120° around the side of the sphere.

Figure 7:
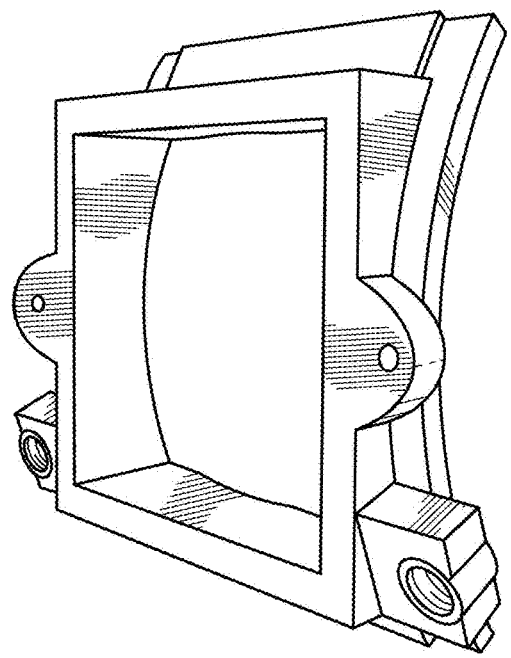
FIG. 7 illustrates a cart.

In some embodiments, track 108 is configured to house cart 104. In other embodiments, the edges of the cart can slot into/onto the track and move freely about the track. Cart 104 can house a light source. FIG. 7 illustrates cart 104 where the light source attaches. Cart 104 as illustrated in FIG. 7 can be used in a light diffusing device configured to attach to a LI-COR Biosciences LI-6800 portable gas infrared gas analyzer. The light source can be a semiconductor light source. In some embodiments, the light source is a light-emitting diode (LED). The cart can house a light source at any position along the track. The track can be open and have a groove that sits above the edge of the sphere for the cart to run through as illustrated in FIG. 2. The cart itself can have a square opening similar to the opening that attaches to the support plate of a leaf chamber of the gas analyzer. In some embodiments, the square opening of the cart can have adjustable screw 114, as illustrated in FIG. 1, which can be tightened to hold the cart at a specific position along the track. In other embodiments, the cart can include one or more adjustable screws. In some embodiments, the cart includes 1, 2, 3, or 4 screws. The screws can be adjustable. The cart can have any opening configured to attach to a light source. In some embodiments, the cart includes a screw that is tightened against the sphere to hold it in place in its desired location along the track. As illustrated in FIG. 1, cart 104 is placed on track 108 of sphere 102 near the top portion of track 108. In some embodiments, cart 104 can be placed anywhere along track 108, such as, but not limited to, at or near the top of the track, at or near the middle of the track, or at or near the bottom of the track.

The cart having the light source can slide onto the track at any location. The ability to slide the light source anywhere along the track allows for changing the distribution of the angles of the light striking the leaf surface. Unlike previous spheres which only allow for two distributions of angles of light, e.g. primarily direct and primarily diffuse, the devices claimed herein can generate distributions of angles of light that are intermediate between primarily direct and primarily diffuse. In some embodiments, the track can start at the top of the sphere and continue along the side of sphere ending at or near the bottom of the sphere as illustrated in FIG. 1. The user can adjust the length of the track depending on the user's needs.

The cart can be placed at any angle along the track. In some embodiments, the angle at which the cart is placed on the track, can be, but is not limited to, about 1°, about 2°, about 3°, about 4°, about 5°, about 6°, about 7°, about 8°, about 9°, about 10°, about 11°, about 12°, about 13°, about 14°, about 15°, about 16°, about 17° about 18°, about 19°, about 20°, about 21°, about 22°, about 23°, about 24°, about 25°, about 26° about 27°, about 28°, about 29°, about 30°, about 31°, about 32°, about 33°, about 34°, about 35° about 36°, about 37°, about 38°, about 39°, about 40°, about 41°, about 42°, about 43°, about 44° about 45°, about 46°, about 47°, about 48°, about 49°, about 50°, about 51°, about 52°, about 53°, about 54°, about 55°, about 56°, about 57°, about 58°, about 59°, about 60°, about 61°, about 62°, about 63°, about 64°, about 65°, about 66° about 67°, about 68°, about 69°, about 70°, about 71°, about 72°, about 73°, about 74°, about 75°, about 76°, about 77°, about 78°, about 79°, about 80°, about 81°, about 82°, about 83°, about 84°, about 85°, about 86°, about 87°, about 88°, about 89°, about 90°, about 95°, about 100°, about 105°, about 110°, about 115°, about 120°, about 125°, about 130°, about 135°, about 140°, about 145°, about 150°, about 155°, about 160°, about 165°, about 170°, about 175°, or about 180°.

In other embodiments, the angle at which the cart is placed on the track, can be, but is not limited to, 1°, 2°, 3°, 4°, 5°, 6°, 7°, 8°, 9°, 10°, 11°, 12°, 13°, 14°, 15°, 16°, 17°, 18°, 19°, 20°, 21°, 22°, 23°, 24°, 25°, 26°, 27°, 28°, 29°, 30°, 31°, 32°, 33°, 34°, 35°, 36°, 37°, 38°, 39°, 40°, 41°, 42°, 43°, 44°, 45°, 46°, 47°, 48°, 49°, 50°, 51°, 52°, 53°, 54°, 55°, 56°, 57°, 58°, 59°, 60°, 61°, 62°, 63°, 64°, 65°, 66°, 67°, 68°, 69°, 70°, 71°, 72°, 73°, 74°, 75°, 76°, 77°, 78°, 79°, 80°, 81°, 82°, 83°, 84°, 85°, 86°, 87°, 88°, 89°, 90°, 95°, 100°, 105°, 110°, 115°, 120°, 125°, 130°, 135°, 140°, 145°, 150°, 155°, 160°, 165°, 170°, 175°, or 180°.

In other embodiments, the angle at which the cart is placed on the track, can be, but is not limited to, about 1°-10°, about 10°-20°, about 20°-30°, about 30°-40°, about 40°-50°, about 50°-60°, about 60°-70°, about 70°-80°, about 80°-90°, about 90°-100°, about 100°-110°, about 110°-120°, about 120°-130°, about 130°-140°, about 140°-150°, about 150°-160°, about 160°-170°, or about 170°-180°.

Figure 3:
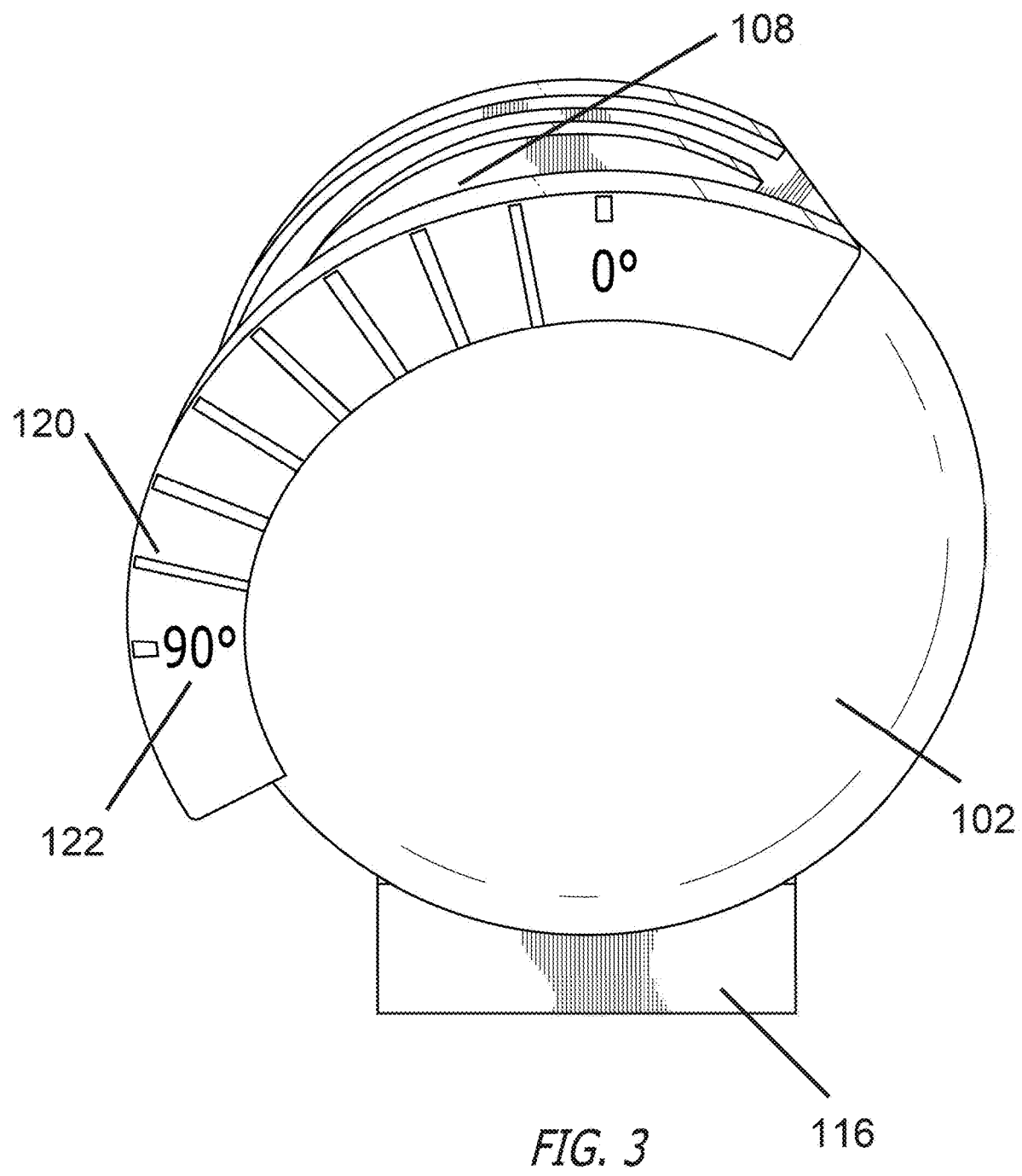
FIG. 3 illustrates a side view of a light diffuser device described herein.

In some embodiments, the angle can be denoted along the side of the track by a notch, a number, a tick mark, and/or a combination thereof. In other embodiments, the angle(s) can be denoted along the side of the track by a combination of tick marks and numbers as illustrated in FIG. 1. A combination of tick marks 120 and numbers 122 can be seen on one side of track 108 in FIGS. 1, 2 and 3. The combination of tick marks can be located on the outer side of the track, as illustrated by FIGS. 1, 2, and 3. In some embodiments, the combination of tick marks and numbers can be on one side of the track. In other embodiments, the combination of tick marks and numbers can be on both sides of the track. The combination of tick marks and numbers can be equivalent to a range of between about 0° to about 45°, between about 0° to about 90°, between about 10° to about 90°, between about 0° to about 120°, between about 10° to about 120°, between about 0° to about 180°, or between about 10° to about 180°.

In other embodiments, as illustrated in FIG. 1, track 108 can span 120° while the combination of tick marks and numbers denoting angles only span from 0° to 90°. In some embodiments, the track can span a greater length along the perimeter of the sphere in comparison to the angles denoted by tick marks and/or numbers.

Figure 8:
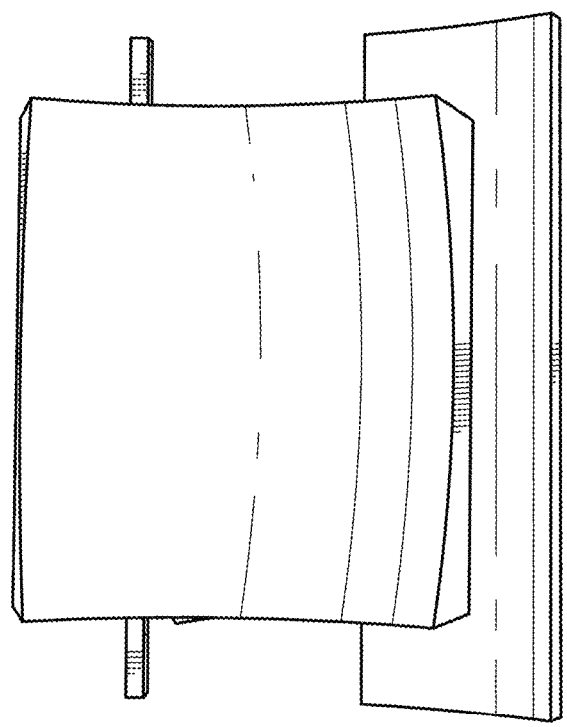
FIG. 8 illustrates an interior view of a large plate.
Figure 9:
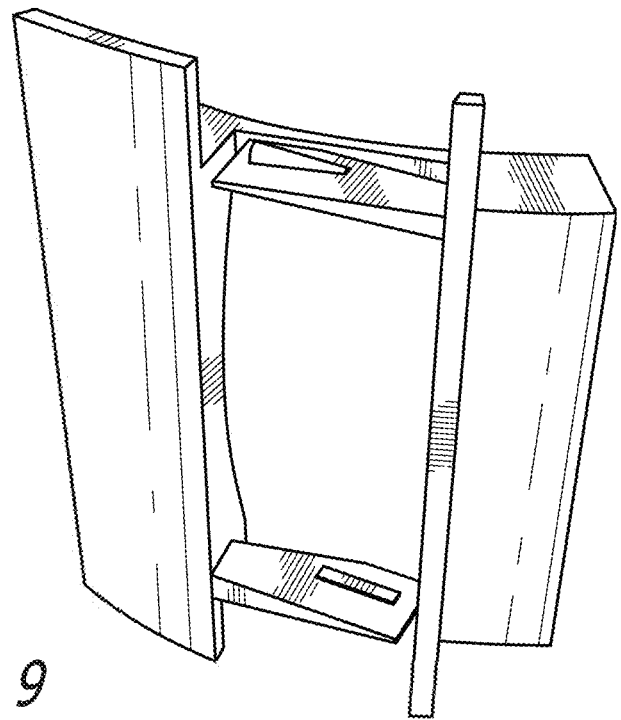
FIG. 9 illustrates an angled view of the exterior of a large plate.
Figure 10:
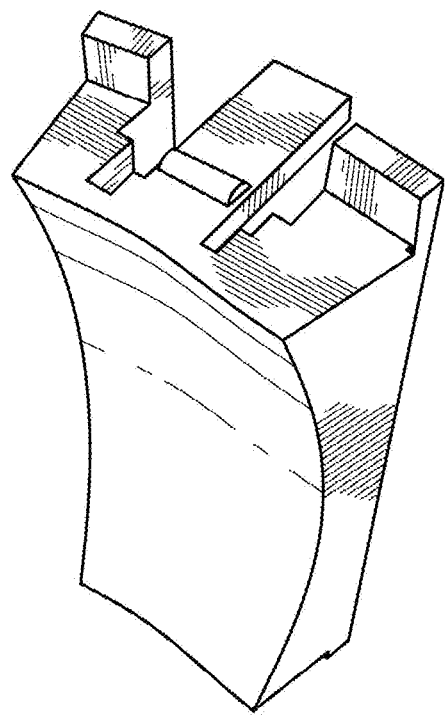
FIG. 10 illustrates an angled view of the interior of a small plate.
Figure 11:
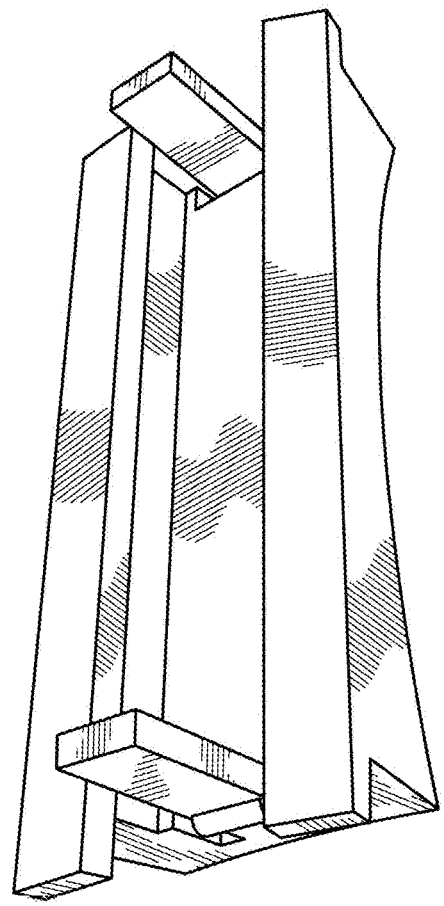
FIG. 11 illustrates an angled view of the exterior of a small plate.

The light diffuser device can comprise one or more plates. In some embodiments, the light diffuser device can comprise at least one or more plates. In other embodiments, the light diffuser device can comprise 1, 2, 3, 4, 5, 6, 7, 8, 9, or 10 plates. The plates can be of varying sizes, such as, but not limited to, a small plate, a large plate, or a combination thereof. FIG. 8 illustrates a view of the interior of a large plate that can be used to close the sphere. The sphere can be closed by fitting a plate on an exposed location of the track. FIG. 9 illustrates an angled view of the exterior of a large plate that can be used to close the sphere. FIG. 10 illustrates an angled view of the interior of a small plate that can be used to close the sphere. FIG. 11 illustrates an angled view of the exterior of a small plate used to close the sphere.

In some embodiments, the plates can be cover plates. In other embodiments, the plates can fit into/onto the track to seal the exposed locations along the track. Each plate can have a smoothed and rounded surface that fits the interior curvature of the sphere and locks into/onto the track with small notches on either side. In other embodiments, plates and/or the cart can be placed/fitted onto track utilizing the notched spacing on the track as illustrated in FIG. 2. The track and the notched spacing on the track that can guide the positioning of the cart housing the light source from 0° to 90° angles is illustrated in FIG. 3.

In some embodiments, the plates can also include small overlapping wings on the exterior to help reduce the loss of light through any cracks between the plates. In other embodiments, when the plates are in place the cart cannot move freely about the track but rather is confined to its position on the track. In some embodiments, the plate(s) fit into/onto the track to seal the exposed locations along the track, thereby closing the sphere. By closing the sphere the plates can prevent the loss of light out of the leaf which would otherwise be reflected and strike the surface of the leaf.

FIG. 1 illustrates a light diffuser sphere comprising a cart configured to house a light source on top of the track, and plates in position on the track. The track runs around the perimeter of the sphere and incorporates the track seen in FIG. 2. Plates shown in FIG. 1 can be removed, the light source then repositioned along the track and the plates returned to maintain closure of the sphere.

In some embodiments, a light diffuser sphere described herein can be manufactured using material, such as, but not limited to, plastic, lightweight metal, and/or a combination thereof. The plastic can be composed of acrylonitrile butadiene styrene (ABS), polylactic acid polymer (PLA), nylon, carbon fiber composite, and/or a combination thereof. In some embodiments, the light diffuser device is composed of PLA and 3D printed. The sphere can be printed as a single piece, with the accessory interlocking plates and cart printed separately. A plastic polymer can be useful for manufacturing the light diffuser devices descried herein due to its strength and durability, as well as its light weight compared to metal-based alternatives. This can be important because the leaf gas analyzer is intended to be highly portable (e.g. field or greenhouse research) and thus this component should similarly have the ability to be easily transported to remote and difficult locations. In some embodiments, the inside of the sphere can be coated in a highly reflective paint. In some embodiments, the inside of the sphere can be primed and then painted with highly-reflective white paint. In other embodiments, the highly-reflective paint is the Avian-B White Reflectance Coating purchased from Edmund Optics. This highly-reflective paint coating includes pure barium sulfate, and is mixed with 95% ethanol and 5% methanol alcohol before being applied to the inside of the sphere. Once mixed, the coating is sprayed onto the inside of the sphere in a series of 15-20 total layers. In some embodiments, the coating can be sprayed on the inside of the sphere in a series of about 2, about 4, about 6, about 8, about 10, about 12, about 14, about 16, about 18, about 20, about 22, about 24, about 26, about 28, about 30, 2, 3, 4, 5, 6, 7, 8, 10, 11, 12, 13, 14, 15, 16, 17, 18, 19, 20, 21, 22, 23, 24, 25, 26, 27, 28, 29, or 30 layers.

In some embodiments, the sphere can have light emanate from the light source head (typically generated by LEDs), which then reflects off the walls of the sphere eventually arriving at the opening that attaches to the gas analyzer. As the light moves along the track from directly above the opening, configured to attach to the gas analyzer, to the side of the sphere, the light changes from predominantly direct to predominantly diffuse. By having a track, the user can control the proportion of the light that is direct or diffuse. The inside reflective coating allows for the majority of the emitted radiation to reach the opening where a leaf would be located.

The light diffuser sphere devices described herein allow researchers to quickly and easily control a variable that was previously impossible with traditional infrared gas analysis equipment. Plant photosynthesis responds to changes in the angle of light, yet the majority of work to date does not allow the researcher to control this variable. The creation of the diffusing sphere described herein for portable infrared gas analyzers allows the user to understand how leaf-level gas exchange responds along this axis of variation. This can directly lead to an expansion of research addressing how plants and ecosystems respond to changes in light environment in the face of anthropogenic global change (e.g. changes in cloudiness or increases in air pollution).

There are no alternative ways to control the delivery of the proportion of direct versus diffuse light to an infrared gas analyzer. Thus, it provides great value for researchers intending to study this parameter.

The light diffuser devices described herein can have an opening that allows for the delivery of variable proportions of diffuse light, for example a cart with a light source, that integrates directly with a portable infrared leaf gas analyzer, and directly utilizes the light source that comes with the leaf gas analyzer.

Methods of using the devices described here, can include, but are not limited to, attaching a light source to a cart, and sliding the cart onto a track of a sphere. The cart can be slid to the desired position, and held in place with a tightened screw. In some embodiments, the desired position is dictated by the distribution of angles of light that the user wishes to obtain. After the cart is slid to the desired position and held in place with a tightening screw, the open space (i.e. exposed locations) along the track can be sealed using one or more plates. The sphere is then connected to a leaf chamber of a portable infrared gas analyzer. The light source is then set to its desired intensity and spectra. The leaf is then allowed to equilibrate those conditions, and the leaf gas exchange is measured using the gas analyzer.

In some embodiments, the position of the light source can be changed to a new desired position. In such case, the plates are removed, the screw is loosened, and the cart is removed from the track. The cart can then be placed and/or slid onto the track at another desired position. The screw is then tightened once again, the plates are placed back onto the track at the exposed location(s), and then another gas exchange measurement can be made with the light coming from this distribution of angles.

In some embodiments, a light diffuser device comprises a sphere having at least two openings, wherein one opening includes a track and the other opening includes a base having supports; one or more plates positioned on the track; and a cart including a light source positioned on the track. In other embodiments, the base having supports is configured to attach to a gas analyzer. The base having supports is secured to the sphere via a fastener. The base having supports slides onto a leaf chamber of the gas analyzer. The gas analyzer is an infrared, portable gas analyzer.

In some embodiments, the cart includes the light source and is positioned at an angle. The cart including the light source is secured to the track via a fastening mechanism. In some embodiments, the cart is positioned at an angle of 67.5°. In other embodiments, the cart is positioned at an angle of 90°. In some embodiments, the cart is positioned at an angle of 0°. In some embodiments, the angle is denoted by a combination of tick marks and numbers. In other embodiments, the combination of tick marks and numbers are located on an outer portion of one side of the track.

In some embodiments, the track is rectangular and runs 120° around the side of the sphere. The light source is a light-emitting diode. In other embodiments, one or more plates are positioned on the track to close the sphere. The one or more plates are positioned on the track at exposed locations to close the sphere.

In some embodiments, the outer diameter of the entire sphere can be about 10 cm, about 11 cm, about 12 cm, about 13 cm, about 14 cm, about 15 cm, about 16 cm, about 17 cm, about 18, about 19 cm, about 20 cm, about 20.1 cm, about 20.2 cm, about 20.3 cm, about 20.4 cm, about 20.5 cm, about 20.6 cm, about 20.7 cm, about 20.8 cm, about 20.9 cm, about 21 cm, about 22 cm, about 23 cm, about 24 cm, about 25 cm, about 26 cm, about 27 cm, about 28 cm, about 29 cm, about 30 cm, 10 cm, 11 cm, 12 cm, 13 cm, 14 cm, 15 cm, 16 cm, 17 cm, 18, 19 cm, 20 cm, 20.1 cm, 20.2 cm, 20.3 cm, 20.4 cm, 20.5 cm, 20.6 cm, 20.7 cm, 20.8 cm, 20.9 cm, 21 cm, 22 cm, 23 cm, 24 cm, 25 cm, 26 cm, 27 cm, 28 cm, 29 cm, 30 cm, between about 10 cm and about 21 cm, between about 15 cm and about 25 cm, between about 15 cm and about 30 cm. In some embodiments, the outer diameter of the entire sphere is 20.2 cm.

In other embodiments, the inner diameter of the entire sphere can be about 10 cm, about 11 cm, about 12 cm, about 13 cm, about 14 cm, about 15 cm, about 16 cm, about 17 cm, about 18, about 19 cm, about 19.1 cm, about 19.2 cm, about 19.3 cm, about 19.4 cm, about 19.5 cm, about 19.6 cm, about 19.7 cm, about 19.8 cm, about 19.9 cm, about 20 cm, about 21 cm, about 22 cm, about 23 cm, about 24 cm, about 25 cm, about 26 cm, about 27 cm, about 28 cm, about 29 cm, about 30 cm, 10 cm, 11 cm, 12 cm, 13 cm, 14 cm, 15 cm, 16 cm, 17 cm, 18, 19 cm, 20 cm, 20.1 cm, 20.2 cm, 20.3 cm, 20.4 cm, 20.5 cm, 20.6 cm, 20.7 cm, 20.8 cm, 20.9 cm, 21 cm, 22 cm, 23 cm, 24 cm, 25 cm, 26 cm, 27 cm, 28 cm, 29 cm, 30 cm, between about 10 cm and about 21 cm, between about 15 cm and about 25 cm, between about 15 cm and about 30 cm. In some embodiments, the inner diameter of the entire sphere is 19.2 cm.

In other embodiments, the opening where the light source sits can be about 3 cm, about 4 cm, about 5 cm, about 6 cm, about 7 cm, about 8 cm, about 9 cm, about 10 cm, about 11 cm, about 12 cm, about 13 cm, about 14 cm, about 15 cm, 3 cm, 4 cm, 5 cm, 6 cm, 7 cm, 8 cm, 9 cm, 10 cm, 11 cm, 12 cm, 13 cm, 14 cm, 15 cm, between about 0.5 cm and about 9 cm, between about 1 cm and about 10 cm, or between about 5 cm and about 15 cm wide, and can run about 16 cm, about 17 cm, about 18, about 19 cm, about 20 cm, about 21 cm, about 22 cm, about 23 cm, about 24 cm, about 25 cm, about 26 cm, about 27 cm, about 28 cm, about 29 cm, about 30 cm, 16 cm, 17 cm, 18, 19 cm, 20 cm, 21 cm, 22 cm, 23 cm, 24 cm, 25 cm, 26 cm, 27 cm, 28 cm, 29 cm, 30 cm, between about 10 cm and about 25 cm, or between about 15 cm and about 30 cm long around the edge of the sphere. In some embodiments, the opening where the light source sits is 8 cm wide and runs approximately 23 cm long around the edge of the sphere.

In other embodiments, the width of the track where the light cart sits can be about 2 cm, about 3 cm, about 4 cm, about 5 cm, about 6 cm, about 7 cm, about 8 cm, about 9 cm, about 10 cm, 1 cm, 2 cm, 3 cm, 4 cm, 5 cm, 6 cm, 7 cm, 8 cm, 9 cm, 10 cm, between about 0.5 cm and about 10 cm, between about 1 cm and about 5 cm, or between about 1 cm and about 3 cm wide.

In some embodiments, the at least one opening of the sphere where the gas analyzer attaches can be about 8 cm×about 8 cm, about 7 cm×about 7 cm, about 6 cm×about 6 cm, or about 5 cm×about 5 cm opening. In other embodiments, the at least one opening of the sphere where the gas analyzer attaches is an 8 cm×8 cm opening. In other embodiments, the supporting square/base around the at least one opening of the sphere where the gas analyzer attaches can be about 13 cm×about 9.5 cm. In some embodiments, the supporting square/base around the at least one opening of the sphere where the gas analyzer attaches is 13 cm×9.5 cm.

In some embodiments, a method of using a light diffuser device comprises a sphere having at least two openings, wherein one opening includes a track and the other opening includes a base having supports; positioning a cart including a light source on the track at a desired angle; securing the cart including the light source to the track via a securing mechanism; sealing exposed locations of the track with one or more plates; and positioning the base having supports onto a leaf chamber of a gas analyzer. In other embodiments, the method further comprises setting the light source at a desired intensity and spectra.

In some embodiments, the method includes a leaf in the leaf chamber of the gas analyzer which equilibrates the conditions and a leaf gas exchange is measured using the gas analyzer. The securing mechanism occurs via a fastener. The base having supports is secured to the sphere via a fastener.

EXAMPLES

Example 1. Diffuse light and wetting differentially affect tropical tree leaf photosynthesis Most ecosystems experience frequent cloud cover resulting in light that is predominantly diffuse rather than direct. Moreover, these cloudy conditions are often accompanied by rain that results in wet leaf surfaces. Despite this, the understanding of photosynthesis is built upon measurements made on dry leaves experiencing direct light.

Using a modified gas exchange setup, the effects of diffuse light and leaf wetting were measured on photosynthesis in canopy species from a tropical montane cloud forest.

It is demonstrated that significant variation in species-level response to light quality independent of light intensity. Some species demonstrated 100% higher rates of photosynthesis in diffuse light, and others had 15% greater photosynthesis in direct light. Even at lower light intensities, diffuse light photosynthesis was equal to that under direct light conditions. Leaf wetting generally led to decreased photosynthesis, particularly when the leaf surface with stomata became wet; however, there was significant variation across species.

Ultimately, it is demonstrated that ecosystem photosynthesis is significantly altered in response to environmental conditions that are ubiquitous. The results help to explain the observation that net ecosystem exchange can increase in cloudy conditions and can improve the representation of these processes in Earth systems models under projected scenarios of global climate change.

The understanding of photosynthesis is predominantly based on measurements made on dry leaves receiving direct light. But nearly all ecosystems spend considerable time in cloudy conditions, which result in diffuse light. When these clouds are accompanied by precipitation events, leaves and canopies become wet. Understanding the relationship between photosynthesis and environmental conditions is critical for modeling ecosystem primary productivity, and research to date has considered many of these variables, such as temperature, light intensity, $CO_2$ concentration and soil moisture. Explicit tests of the effects of diffuse light or leaf wetting on leaf or canopy photosynthesis are exceedingly limited, with only 11 studies in the last 10 years. In addition, many of these are conducted in highly controlled laboratory and glasshouse settings which may not reflect the complex environmental conditions and physiological responses that occur in the field.

Light generally arrives to the canopy in direct, parallel beams but is scattered as it encounters particles in the air. If enough radiation is scattered, then the apparent radiation at the plant canopy is no longer direct, but rather predominantly diffuse light. For plant canopies, this most commonly occurs when clouds and aerosols scatter radiation. Here, diffuse or direct light is defined as conditions where the majority of light arrives in one or the other form, but note that any environmental condition has some proportion of both forms. At ecosystem scales, diffuse light can increase primary productivity. This increase has largely been ascribed to light penetrating deeper into the canopy and reaching more leaf surface area. Only a few studies have explored how diffuse light might alter photosynthesis at the leaf level. These studies have concluded that, at the same total light, diffuse light inhibits photosynthesis by 10-20%. Thus, leaf-level data suggest that diffuse light decreases photosynthesis, whereas ecosystem studies find that it increases productivity. Understanding the effects of diffuse light on primary productivity is critical for constraining carbon (C) cycling, particularly given that climate change models project an increase to cloud cover and aerosols, which will lead to an increase in diffuse light conditions.

In addition to changing the quality of light, clouds often bring precipitation, leading to wet canopies. Plants in tropical forest ecosystems experience leaf wetting an average of 174 days every year; however, it is assumed that limited C exchange occurs when the canopy is wet. The presumed mechanism for this reduction is that water on leaf surfaces creates a physical barrier for the uptake of $CO_2$ and therefore limits photosynthesis. However, this assumes that a film of water entirely covers most stomata during a wetting event. Thus, at the leaf scale, whether there is a reduction in photosynthesis as a result of this physical barrier will be species- and context-dependent based on wettability of leaf surfaces and spatial distribution of stomata. At the ecosystem scale, leaf wetness has been shown to reduce primary productivity and net ecosystem exchange. However, it is challenging to isolate the effect of leaf wetness relative to changes in the intensity and quality of light. In addition, eddy covariance, the primary methodology for measuring net ecosystem exchange, does not work under wet conditions and this limits our understanding of ecosystem primary productivity during leaf wetting events.

Nowhere on Earth does the limited understanding of the effects of cloudy and wet environmental conditions on photosynthesis and ecosystem primary productivity pose more of a problem than in tropical forests. Tropical forests account for 50% of the 2.4±0.4 Pg of C stored annually by terrestrial vegetation, despite experiencing frequent cloud cover and wetting. Thus, the limited mechanistic understanding of photosynthetic C uptake during these periods challenges our ability to estimate both current and future global C budgets.

The simple yet fundamental question: "how do photosynthetic rates change when the angle of light changes and leaves are wet?" is addressed. Understanding the effects of these common environmental conditions on C assimilation could improve our estimations of ecosystem primary productivity and reveal new insights into how species maximize photosynthesis given different environmental conditions. Using a tropical rainforest system that commonly experiences these climate conditions, there are three objectives: to determine if there are species-specific responses to diffuse light conditions and canopy wetting; to test if these responses are driven by morphological and physiological characteristics that influence light penetration, leaf wetting patterns, and C uptake; and to place the results in the context of common environmental conditions in order to understand the implications for ecosystem primary productivity. Research to date leads to the hypotheses that diffuse light and leaf wetting both lead to a consistent and demonstrable decrease in photosynthesis; however, results clearly demonstrate that photosynthetic responses to cloudy and wet conditions are species-specific. Moreover, shown herein is that increases in photosynthesis under diffuse light can help explain ecosystem studies showing similar patterns and contribute to improving the representation of these processes in Earth systems models.

Materials and Methods

Study Site and Sampling

The study was conducted in a tropical montane cloud forest on the Pacific slope of the Cordillera de Tilarán mountains in Monteverde, Costa Rica (10°17'43"N, 84°47'37"W, 1532 m asl). Trees were sampled from within a 4 hectares (ha) long-term forest dynamics plot in the Monteverde Cloud Forest Reserve. The plot is described as old growth lower montane wet forest. The mean annual temperature is 18.8° C., the mean annual rainfall is 2519 mm, and the average annual relative humidity is 97%. Climate is relatively aseasonal, although there is a dry season extending from February to May. Rainfall during the dry season decreases, but fog and wind-driven horizontal precipitation persists and leads to frequent leaf wetting.

Previous studies in tropical montane cloud forests suggest that solar radiation can be reduced by 10-66% during fog and wind-driven precipitation events. At the study site, it was found that midday photosynthetically active radiation (1200-1400 solar time) is >410 μmol m$^{-2}$ s$^{-1}$ 81% of the time. The interquartile range of the distribution spans from 496 to 1381 μmol m$^{-2}$ s$^{-1}$. Although there is no precise data on the fraction of time in direct and diffuse light, the frequency of clouds from remote sensing products is known. A remote sensing product was used to demonstrate that clouds were frequently observed in daytime images during both the wet (89±9%) and dry (52±11%) seasons. It was found that cloudy periods typically increased the diffuse index>0.7 compared with <0.3 during sunny conditions. From these data, it can be concluded that diffuse light conditions are a predominant feature in this ecosystem, and that light intensity is at or above the light compensation points of species for 81% of midday hours.

Eight common canopy tree species using plot census data on basal area and number of stems collected on all individuals >30 cm diameter at breast height (Table 1) were selected. The species were *Cecropia polyphlebia* Donn. Sm., *Conostegia rufescens* Naudin, *Elaeagia auriculata* Hemsl., *Ficus* spp., *Heliocarpus americanus* L., *Meliosma vernicosa* (Liebm.) Griseb., *Ocotea meziana* C. K. Allen, and *Ocotea tonduzii* Standl. All species are considered canopy-emergent (although they have different successional patterns) and were only sampled if the tree was mature and sun-exposed. Sufficient individuals from a single species of the genus *Ficus* were not able to be located, which accounts for a high proportion of the plot basal area but is low in abundance. Branch samples were collected from five to seven canopy-emergent individuals of each species using a slingshot to secure a branch at least 1 m in length. Once collected, the cut portion of each branch was immediately placed in water and the end of the branch was recut. The branch remained in the field in the water during all gas exchange measurements, and measurements were begun within 1 h of collection.

TABLE 1

List of species used in this study, including the abundance of each species as measured by number of stems and basal area of individuals >30 cm DBH (diameter at breast height) represented within the 4 ha plot in Monteverde, Costa Rica. DBH is the measure of a tree diameter that was standardized at a set height of 1.35 meters off the ground.

| Species | Family | % of stems | % of plot basal area |
|---|---|---|---|
| *Cecropia polyphlebia* | Urticaceae | 6.0 | 4.3 |

TABLE 1-continued

List of species used in this study, including the abundance of each species as measured by number of stems and basal area of individuals >30 cm DBH (diameter at breast height) represented within the 4 ha plot in Monteverde, Costa Rica. DBH is the measure of a tree diameter that was standardized at a set height of 1.35 meters off the ground.

| Species | Family | % of stems | % of plot basal area |
|---|---|---|---|
| Conostegia rufescens | Melastomataceae | 3.7 | 2.7 |
| Elaeagia auriculata | Rubiaceae | 2.3 | 1.7 |
| Ficus spp. | Moraceae | 2.3 | 17.0 |
| Heliocarpus amereicanus | Malvaceae | 2.8 | 2.6 |
| Meliosma vernicosa | Sabiaceae | 4.2 | 3.6 |
| Ocotea meziana | Lauraceae | 5.6 | 4.8 |
| Ocotea tonduzii | Lauraceae | 15.3 | 22.2 |

Photosynthesis Data

Light response curves were performed on dry leaves followed by instantaneous measurements on wet leaves using a portable infrared gas analyzer (Li-Cor 6800; Li-Cor Inc. Lincoln, NE). For wet leaf measurements, only a single instantaneous value was taken, to minimize the amount of time that high concentrations of water vapor were entering the Li-Cor 6800 system. Measurements were made on one fully expanded, mature and healthy leaf between 09:00 and 14:00 h. If stomatal conductance showed signs of decreasing compared with measurements from other individuals as the day progressed, then measurements were stopped and the individual resampled the following day. Light response curves were only measured on dry leaves under direct light and diffuse light separately. Leaves were placed in the 6×6 cm large leaf chamber (Model 6800-13; Li-Cor Inc. Lincoln, NE) with the accompanying red (65%), green (10%), blue (20%) and white (5%) LED light sources and allowed to acclimate at a photosynthetically active radiation (PAR) of 1400 µmol m$^{-2}$ s$^{-1}$ until photosynthesis was stable. The light response curves began at the highest PAR value and subsequently decreased. When transitioning through each measurement, the leaf was allowed to acclimate under new conditions for at least 2 min. Temperature was held at 22° C., $CO_2$ concentration at 400 ppm, and relative humidity at 70% when leaves were dry.

Figure 13:
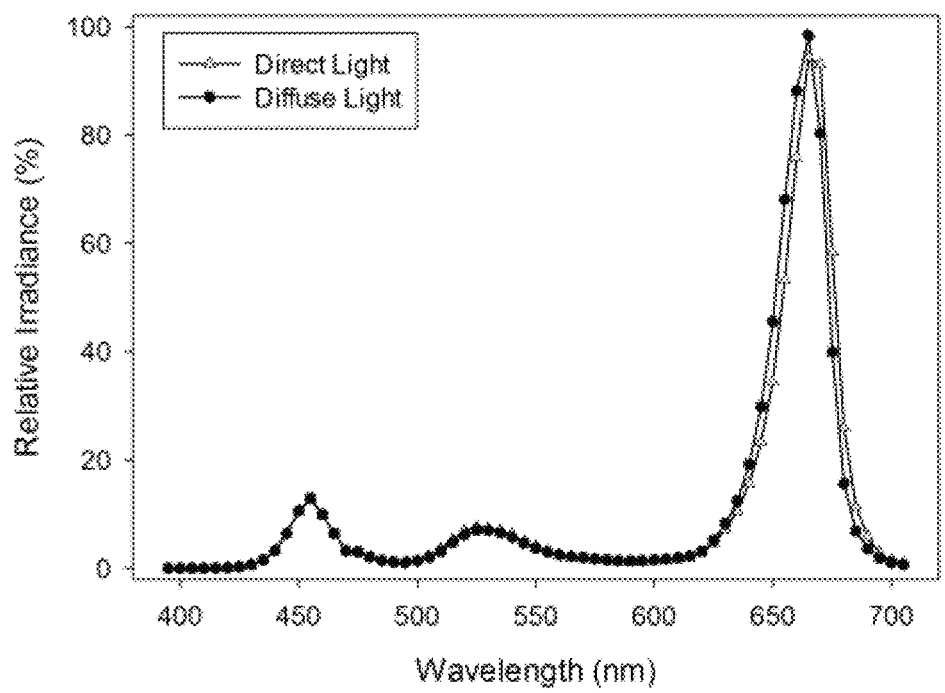
FIG. 13 depicts a spectral analysis of the output of light when the light source was in the direct light position (triangles) and the diffuse light position (circles). All photosynthesis measurement used a combination of the red, green, blue and white LEDs on the 6×6 chamber light source (65% red, 10% green, 20% blue, and 5% white). Spectra were normalized at 665 nm, the peak of the red LED lights used in the light source. All measurements were conducted on a Horiba iHR550 Imaging Spectrometer with the light source in both direct and diffuse positions.
Figure 14:
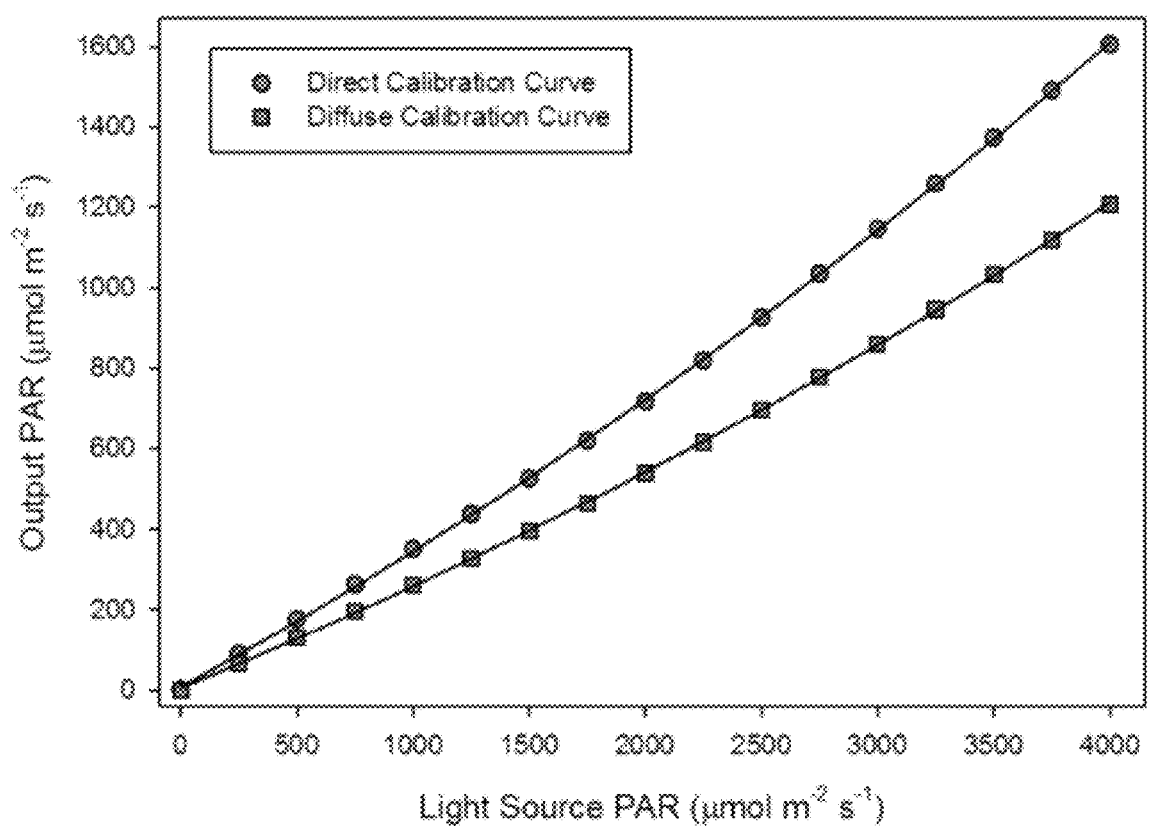
FIG. 14 depicts calibration curves between the programmed value of photosynthetically active radiation (PAR) coming out of the light source and the actual light received in the leaf chamber under the modified direct and diffuse light setup, where an integrating sphere was placed between the light source and the chamber head. Curves were developed by mounting a PAR sensor (LI-190R, LI-COR Biosciences) in the chamber head that normally contains the leaf. The light source PAR was programmed on the LI-6800 and the output PAR read at this mounted sensor. The calibration was done with the light source in both the direct and diffuse positions.
Figure 15A:
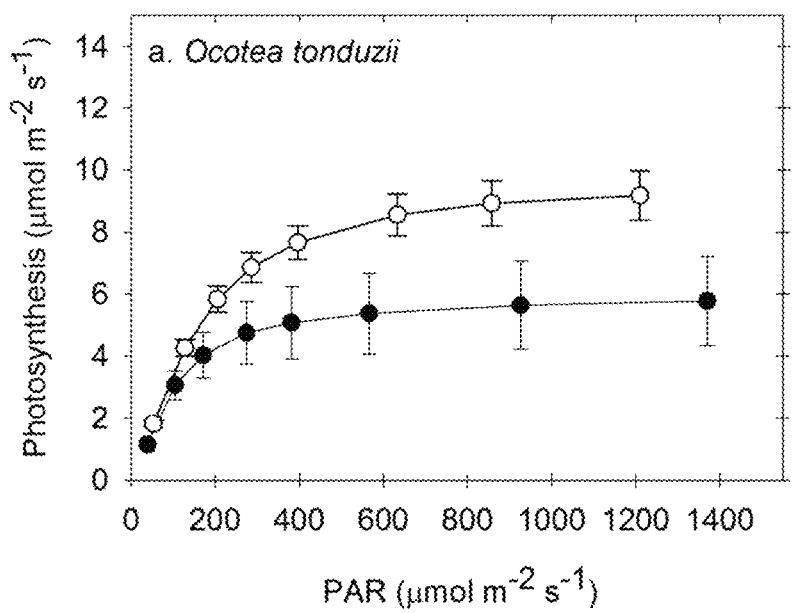
FIGS. 15A-H depict light response curves conducted under direct (closed circles) or diffuse (open circles) light conditions for eight canopy tree species in a tropical forest in Monteverde, Costa Rica (n=5-7 individuals). Each panel (FIGS. 15A-H) represents a different species.
Figure 15B:
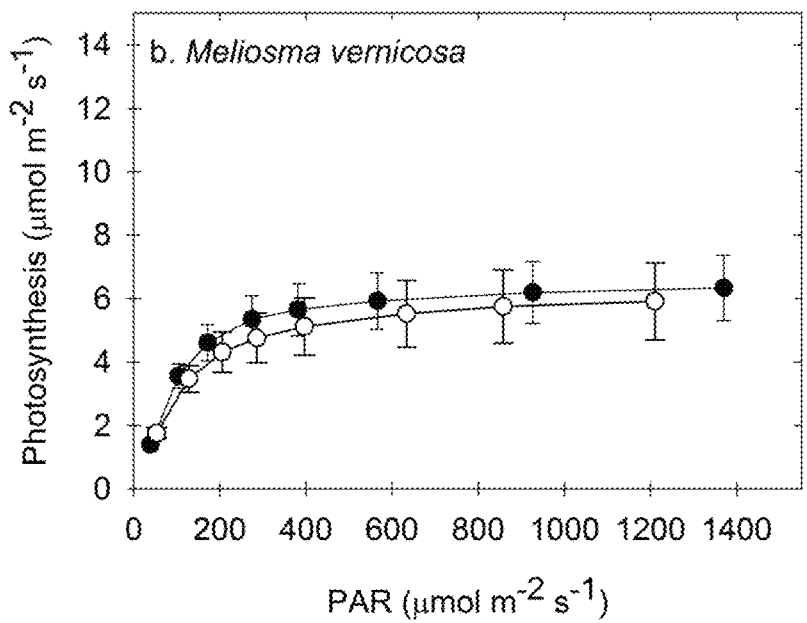
Figure 15C:
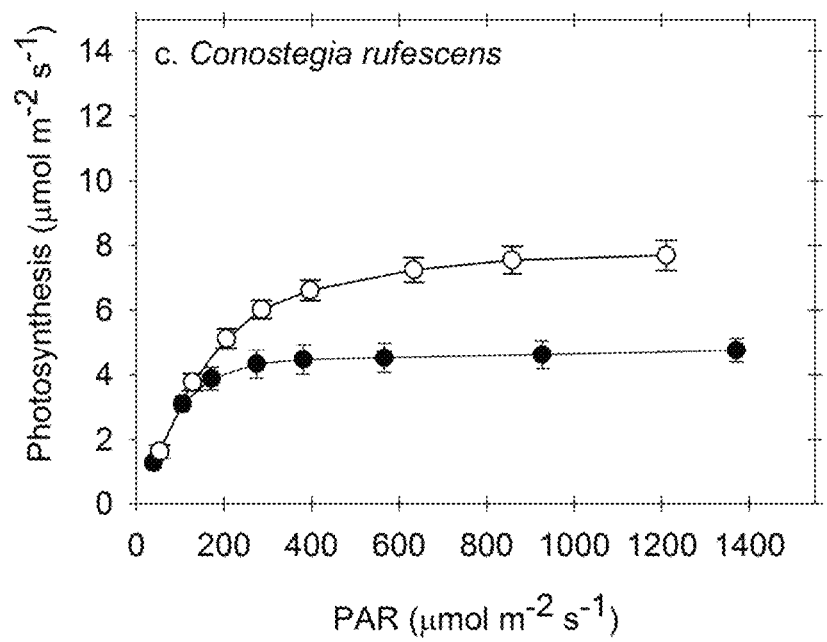
Figure 15D:
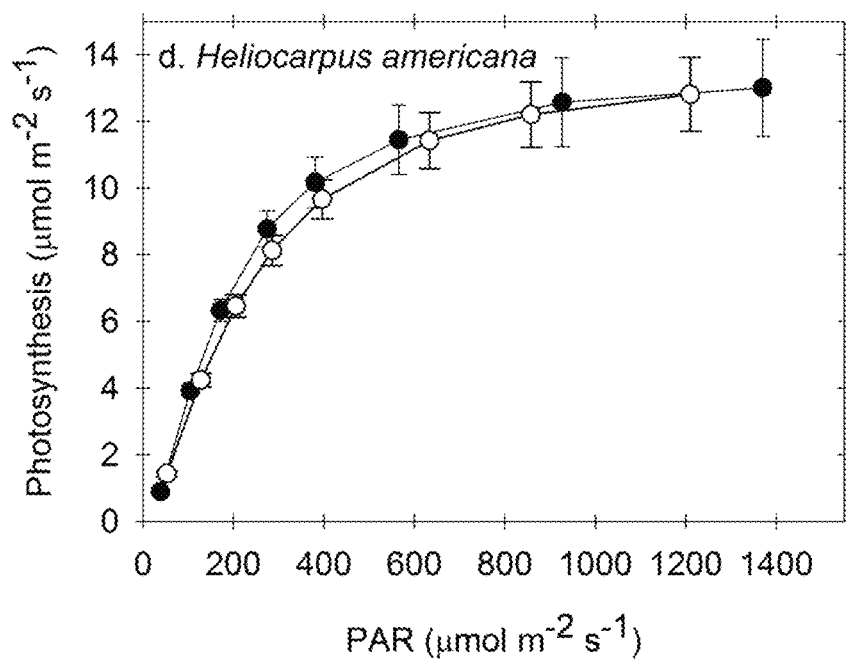
Figure 15E:
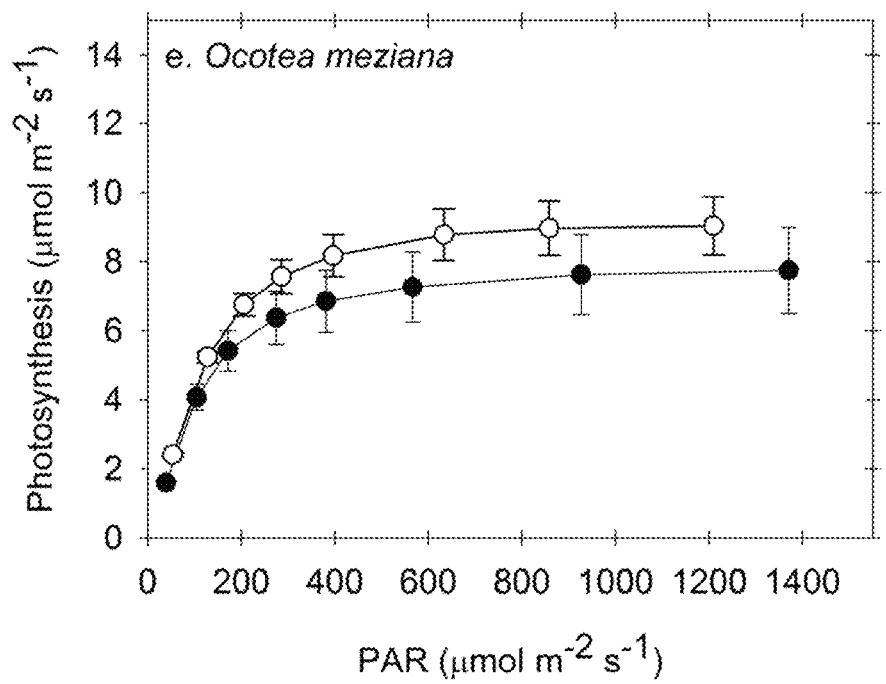
Figure 15F:
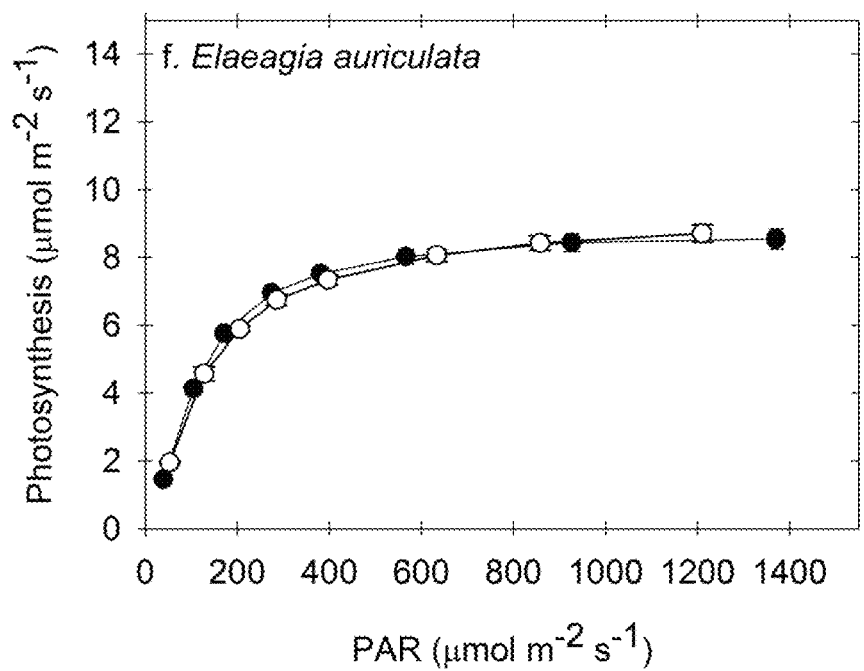
Figure 15G:
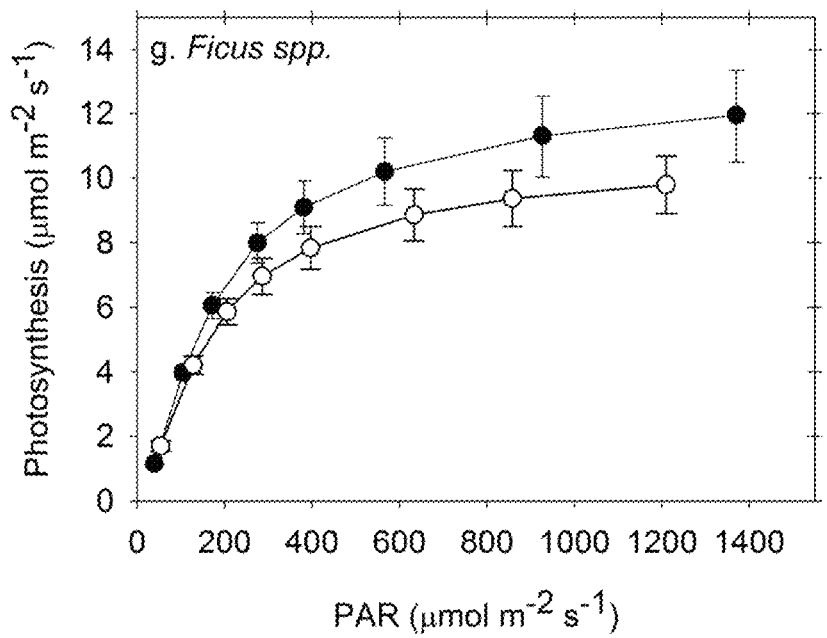
Figure 15H:
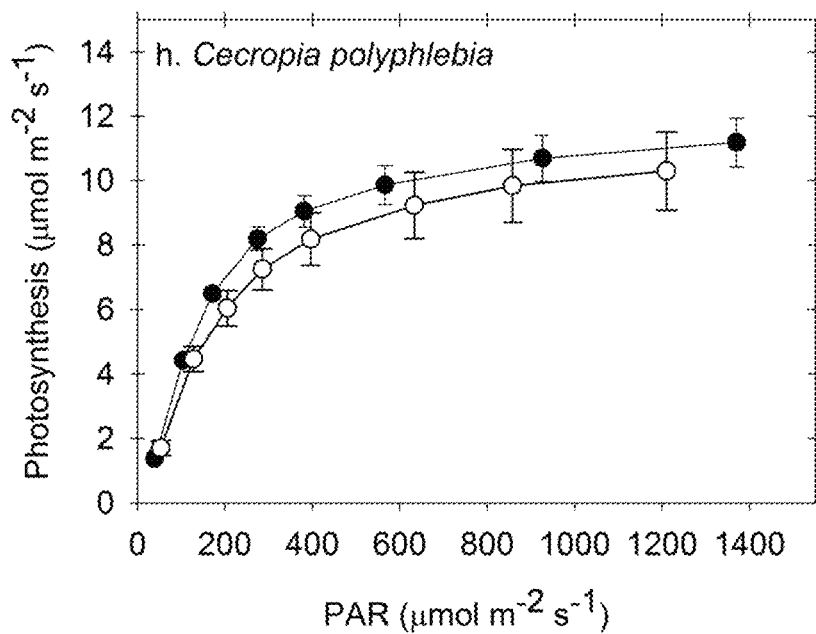

Light response curves under direct and diffuse conditions required a modification to the traditional gas exchange system. To allow for quick changes between direct and diffuse light, an integrating diffuser sphere was constructed with ports/openings for mounting a light source both on top and at the side of the sphere. When the light source was mounted on top of the sphere, light was predominantly direct, whereas mounting on the side port produced largely diffuse light at the leaf surface. When the light is in each position, some proportion of the light will always be direct and some proportion diffuse. Although the direct and diffuse fractions of light in each position were not measured, a protocol was followed which quantified the angle of light in each environmental condition (22° for direct light, 105° for diffuse light). Each port was 6 cm$^2$ to accommodate the large light source and reflective covers were installed on ports not in use. To determine the amount of light that reached the leaf surface with this modified system, calibration curves were conducted in the laboratory to establish the intensity of light leaving the light source and the intensity arriving at the leaf surface (FIG. 14). The visible light spectra were not altered by diffusion was also confirmed (FIG. 13). Curves under direct light had PAR values that corresponded to 1370, 927, 566, 381, 275, 172, 105, and 39 µmol m$^{-2}$ s$^{-1}$. Diffuse light curves had PAR values of 1210, 858, 634, 397, 286, 206, 128, and 53 µmol m$^{-2}$ s$^{-1}$.

Following light response curves on a dry leaf, the leaf was removed from the chamber, misted thoroughly on the adaxial surface, lightly shaken to remove any excess water, and placed back in the chamber in the same position as before. Instantaneous measurements (not light response curves) were then made with wet leaves under direct and diffuse light at 1200 µmol m$^{-2}$ s$^{-1}$ Dry measurements were always conducted before wet measurements because of concerns about the ability to completely dry a leaf again following wetting. Leaves were allowed to stabilize with wet surfaces, which took as long as 20-30 min in some cases. Humidity control was turned off. If areas of the leaf became noticeably dry, the chamber was opened and the leaf sprayed again. Single instantaneous measurements at a PAR of 1210 µmol m$^{-2}$ s$^{-1}$ were taken with the adaxial leaf surface saturated with water under direct and diffuse light. To explore the effects of wetting on photosynthesis as a function of which leaf surface was wet, a follow-up experiment with O. tonduzii leaves from five individuals in the subcanopy was conducted. These leaves were wetted on both the adaxial and abaxial sides following the procedure described earlier.

Measurements on wet leaves inhibited from the reporting of stomatal conductance or transpiration values. Wet surfaces increase the concentration of water vapor exiting the chamber as a result of the combination of both transpiration and evaporation of free water from the leaf surface. This results in erroneous values for transpiration rates, as the two components cannot be partitioned. In addition, the calculation of stomatal conductance also utilizes the concentration of water vapor out of the chamber. The calculation of photosynthesis does not require knowing stomatal conductance, but instead simply utilizes the flow rate and $CO_2$ concentration into and out of the leaf chamber. Therefore, leaf photosynthetic rates were reported, but stomatal conductance and transpiration were excluded.

Leaf Traits

The leaf used for the gas exchange measurements was harvested, placed in a sealed plastic bag with a damp paper towel and transported back to the laboratory for measurement of traits including leaf wetting capacity, leaf thickness, leaf area, specific leaf area and stomatal density.

Leaf wetting capacity was measured as the difference between the mass of a leaf with a dry surface and the mass of the same leaf with water on the adaxial surface. To do this, a fresh mass was measured immediately upon removal from the plastic bag. Then, with the leaf held flat, the leaf was misted using a spray bottle until water was dripping off the leaf. The leaf was then tipped vertically to remove any excess water and the mass was immediately measured. This process was repeated three times for each leaf and the three measurements averaged before determining the intensity of water on the leaf surface. The mass (g) of water on the leaf surface was standardized by the leaf area (cm$^2$).

Leaf thickness was measured at three locations on each leaf and averaged using digital calipers (resolution of 0.001 mm; Mitutoyo Corporation, Kawasaki, Japan). Leaf area was measured by scanning the leaf with a digital scanner and analyzed using IMAGEJ v. 1.51S (National Institutes of Health, Bethesda, MD). Following all these measurements, leaves were dried in a drying oven at 50° C. for c. 1 wk and the dry mass measured to determine specific leaf area and leaf dry matter content. Stomatal density was measured by making stomatal impressions using either clear nail varnish or dental putty (Thermoclone VPS, Fast Set—Superlight Body; Ultradent Products, South Jordan, UT). A thin layer of nail varnish was applied at three locations on each side of each leaf, allowed to dry, removed and mounted onto a glass slide. For species with waxy cuticles or trichomes, dental putty was first applied to the leaf surface and then nail varnish applied to the imprint of the dried dental putty to obtain a transparent impression of the leaf surface. Images were obtained from three locations on each impression using a compound microscope at either ×20 or ×40 magnification. Guard cell length was measured on five stomata per image and the total number of stomata per image was counted.

Data Analysis

The effects of diffuse light and wet leaf conditions on photosynthesis were calculated by calculating the paired difference in photosynthesis measurements for each individual leaf and then determining a species-level mean. The percentage change was calculated in the same manner, by first determining percentage change for each individual. To determine if the response to diffuse light or leaf wetting differed among species, a one-way ANOVA was conducted and compared means using Tukey's honestly significant difference. For light response curves, a nonrectangular hyperbola equation through each individual was fitted as $$A_{net} = \frac{(\varphi PAR + A_{max} - \sqrt{(\varphi PAR + A_{max})^2 - 4k\varphi A_{max} PAR})}{2k} - R_d, \quad \text{(Eqn 1)}$$

where $A_{net}$ is the net photosynthetic rate, $\varphi$ is the quantum yield, PAR is the photosynthetically active radiation, $R_d$ is dark respiration, and k is the convexity factor. The light compensation point was calculated by setting $A_{net}$ to 0, and the light saturation point was calculated as when $A_{net}$ was 85% of $A_{max}$. To compare differences in light response curve parameters (including light compensation point, light saturation point, and quantum yield) for leaves of a given species experiencing direct vs diffuse light, a two-tailed paired-samples t-test was conducted. To determine how the response to diffuse light and leaf wetting varied as a function of morphological or physiological traits, a linear mixed-effects model was used with species as a random effect. All data analysis was conducted in R v.3.4.2 or NIP v.13.2 (SAS Institute, Cary, NC).

Results

Photosynthesis Under Direct and Diffuse Light

Figure 16A:
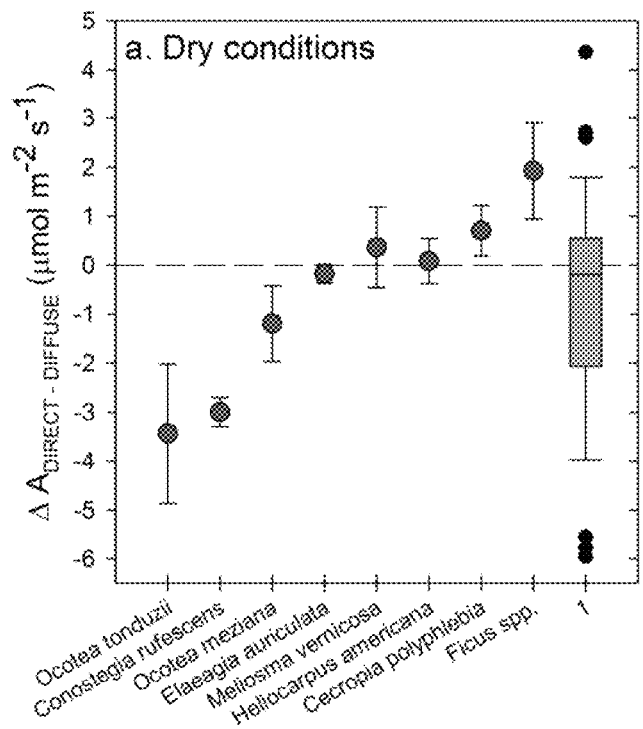
FIGS. 16A-B depict the difference between leaf photosynthesis (A) values observed under direct and diffuse light conditions for eight canopy tree species in a tropical forest in Monteverde, Costa Rica. Measurements were taken at a light intensity of 1210 μmol m$^2$ s$^{-1}$ when leaves were dry (FIG. 16A) or wet (FIG. 16B) and are reported as the absolute difference in photosynthesis.
Figure 16B:
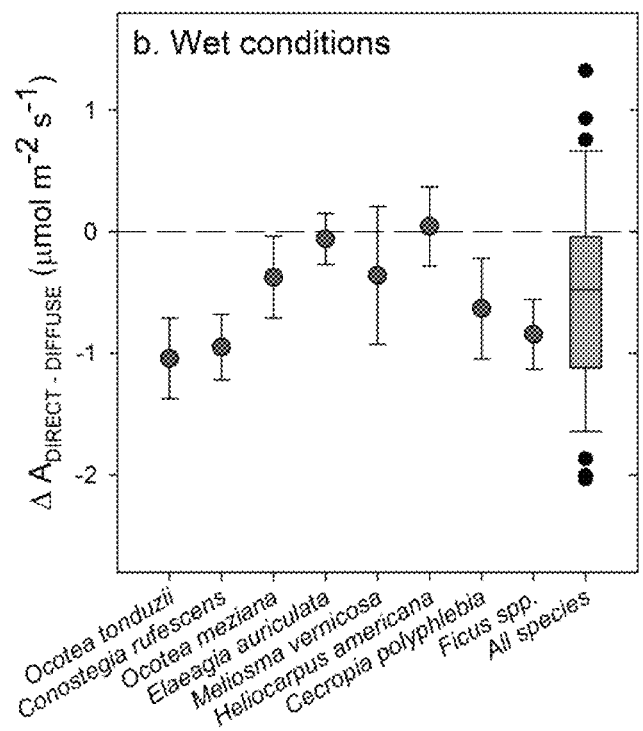

Species demonstrated diverse leaf photosynthetic responses to light quality ($\Delta A_{DIRECT-DIFFUSE}$), with some species having greater photosynthesis under direct conditions and others under diffuse conditions (as depicted in FIGS. 15A-H). Three species had higher $A_{net}$ under diffuse light conditions, two species had higher $A_{net}$ under direct light conditions, and three species showed no significant differences between treatments ($F_{7,31}$=5.58, P<0.001; FIG. 16A dry conditions). For species demonstrating greater photosynthesis in diffuse light, as much as a 3.4±1.0 μmol m$^{-2}$ s$^{-1}$ difference was observed between measurements (O. tonduzii, n=5), which corresponded to a 100% increase in photosynthetic rates. For species with greater photosynthesis under direct light conditions, values tended to be greater by 10-20%. When leaves were wet, photosynthesis in direct light was reduced, which resulted in diffuse light $A_{net}$ being higher for most species when wet as depicted by FIG. 16B.

Diffuse light also resulted in higher light compensation points ($t_{38}$=1.76, P=0.04) and light saturation points ($t_{38}$=2.62, P=0.006), but did not alter the quantum yield of photosynthesis (t 38=0.74, P=0.23; Table 2). While there was an overall effect of diffuse light on light compensation points, there were pairwise differences for only two species. H. americanus had a greater light compensation point under direct light, whereas C. rufescens had a greater light compensation point under diffuse light. Four species (C. rufescens, E. auriculata, H. americanus, and O. tonduzii) had greater diffuse light saturation points, and the other four species showed no significant differences in the post hoc pairwise comparisons. The shifts in light saturation point were large, ranging from 153 to 391 μmol m$^{-2}$ s$^{-1}$. The four species with significant differences in light saturation points included two with significantly greater photosynthesis under diffuse light conditions and two with equal direct and diffuse light photosynthesis. Thus, it is not universally true that it requires more PAR to reach light compensation and saturation under diffuse light conditions.

TABLE 2

Light response curve parameters for eight canopy tree species from a tropical montane forest in Monteverde, Costa Rica.

| | Direct | | | | Diffuse | | | |
|---|---|---|---|---|---|---|---|---|
| Species | $A_{net}$ (μmol m$^{-2}$s$^{-1}$) | φ (μmol CO$_2$ μmol$^{-1}$ photons) | Light compensation point (μmol m$^{-2}$s$^{-1}$) | Light saturation point (μmol m$^{-2}$s$^{-1}$) | $A_{net}$ (μmol m$^{-2}$s$^{-1}$) | φ (μmol CO$_2$ μmol$^{-1}$ photons) | Light compensation point (μmol m$^{-2}$s$^{-1}$) | Light saturation point (μmol m$^{-2}$s$^{-1}$) |
| Cecropia polyphlebia | 11.00 ± 0.76 | 0.087 ± 0.013 | 18.5 ± 1.5 | 630.8 ± 81.6 | 10.29 ± 1.21 | 0.082 ± 0.024 | 23.3 ± 3.7 | 672.7 ± 125.4 |
| Conostegia rufescens | 4.69 ± 0.42 | 0.046 ± 0.006 | 5.0 ± 2.3 | 221.7 ± 39.2 | 7.69 ± 0.47 | 0.042 ± 0.003 | 10.4 ± 3.0 | 494.0 ± 105.2 |
| Elaeagia auriculata | 11.42 ± 0.28 | 0.068 ± 0.010 | 12.6 ± 2.0 | 411.8 ± 59.1 | 10.27 ± 0.42 | 0.094 ± 0.027 | 17.6 ± 2.7 | 586.2 ± 77.0 |
| Ficus spp | 11.71 ± 1.25 | 0.061 ± 0.013 | 17.1 ± 4.2 | 830.7 ± 233.1 | 9.79 ± 0.79 | 0.062 ± 0.015 | 16.8 ± 4.0 | 734.7 ± 183.5 |
| Heliocarpus americana | 12.89 ± 1.42 | 0.056 ± 0.003 | 21.8 ± 2.5 | 649.1 ± 133.2 | 12.81 ± 1.10 | 0.047 ± 0.004 | 19.4 ± 3.2 | 802.9 ± 110.2 |
| Meliosma vernicosa | 6.28 ± 1.03 | 0.072 ± 0.013 | 12.5 ± 1.5 | 342.4 ± 67.4 | 5.91 ± 1.21 | 0.090 ± 0.023 | 14.3 ± 3.2 | 440.2 ± 125.2 |
| Ocotea meziana | 7.73 ± 1.22 | 0.073 ± 0.015 | 10.6 ± 2.4 | 392.9 ± 121.7 | 8.93 ± 0.89 | 0.061 ± 0.006 | 7.8 ± 2.0 | 352.3 ± 41.1 |

TABLE 2-continued

Light response curve parameters for eight canopy tree species
from a tropical montane forest in Monteverde, Costa Rica.

| | Direct | | | | Diffuse | | | |
| --- | --- | --- | --- | --- | --- | --- | --- | --- |
| Species | $A_{net}$ ($\mu$mol m$^{-2}$s$^{-1}$) | $\phi$ ($\mu$mol CO$_2$ $\mu$mol$^{-1}$ photons) | Light compensation point ($\mu$mol m$^{-2}$s$^{-1}$) | Light saturation point ($\mu$mol m$^{-2}$s$^{-1}$) | $A_{net}$ ($\mu$mol m$^{-2}$s$^{-1}$) | $\phi$ ($\mu$mol CO$_2$ $\mu$mol$^{-1}$ photons) | Light compensation point ($\mu$mol m$^{-2}$s$^{-1}$) | Light saturation point ($\mu$mol m$^{-2}$s$^{-1}$) |
| *Ocotea tonduzii* | 5.73 ± 1.44 | 0.058 ± 0.005 | 13.4 ± 3.3 | 349.2 ± 80.0 | 9.18 ± 0.79 | 0.082 ± 0.030 | 16.4 ± 1.7 | 740.6 ± 229.8 |

$A_{net}$, net photosynthetic rate;
$\phi$, quantum yield of photosynthesis.
Leaves were exposed to either direct or diffuse light and the values were derived from curves on five to seven individuals of each species. Data are mean ± SE. All parameters were derived by fitting a non-rectangular hyperbola equation through each individual (Prioul & Chartier, 1977) and averaging the parameters for each species.

Figures 17A, 17B:
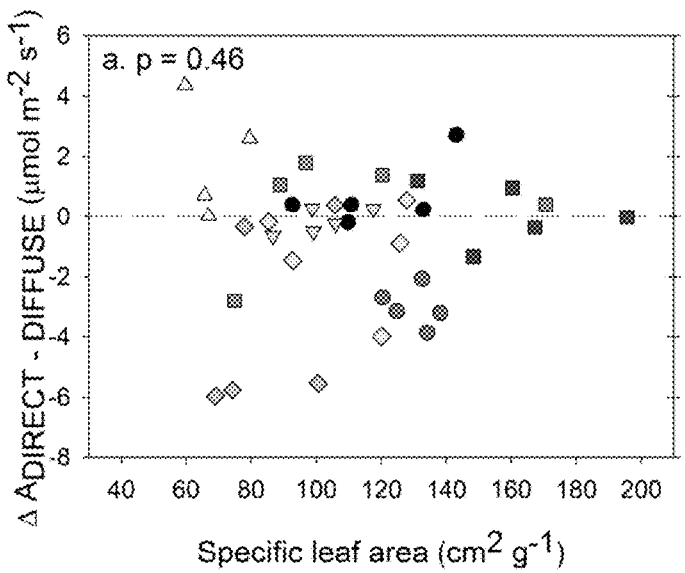
FIGS. 17A-D depict the difference in leaf photosynthesis measured with direct and diffuse light as a function of various parameters.
Figure 17C:
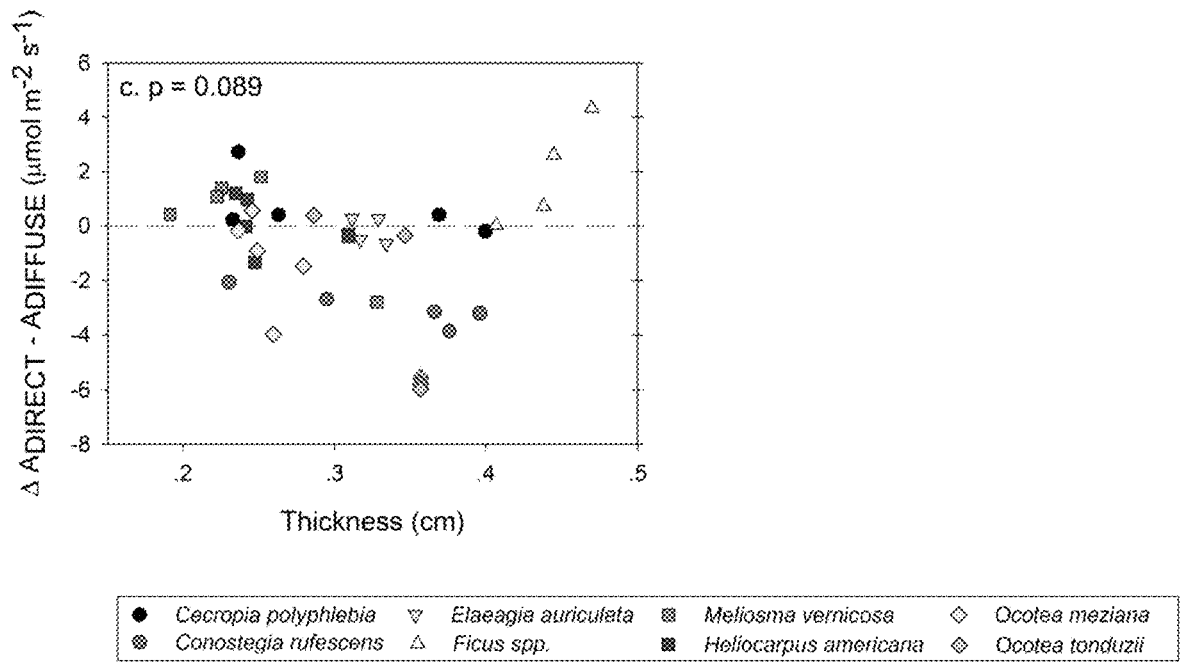
Figure 17D:
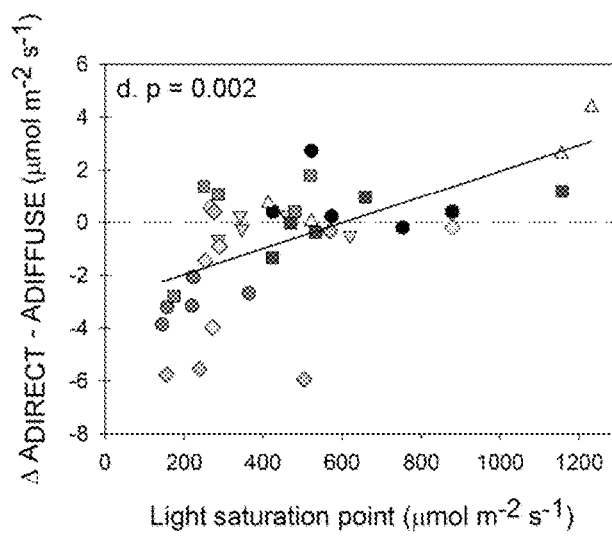

If leaf traits were related to $\Delta A_{DIRECT-DIFFUSE}$ was then explored, but specific leaf area, leaf dry matter content, and leaf thickness did not explain $\Delta A_{DIRECT-DIFFUSE}$ (see FIGS. 17A-C). However, there was a significant negative relationship between $\Delta A_{DIRECT-DIFFUSE}$ and increasing leaf thickness ($F_{1,37}$=14.62; P<0.001, $r^2$=0.31) when *Ficus* spp. was removed. Because of the response of the light saturation points to diffuse light, the relationship between the light saturation point and $\Delta A_{DIRECT-DIFFUSE}$ was also considered, and a significant positive relationship was found (P=0.002, $r^2$=0.60; FIG. 17D). Trait values for all species can be found in Table 3. Table 3 depicts canopy leaf traits measured for eight tree species from a tropical montane forest in Monteverde, Costa Rica. Values are the ±standard error (n=5-7 individuals species$^{-1}$).

light conditions. Thus, species with a lower $A_{net}$ in dry, direct conditions tended to have greater $A_{net}$ in diffuse conditions.

Figure 19A:
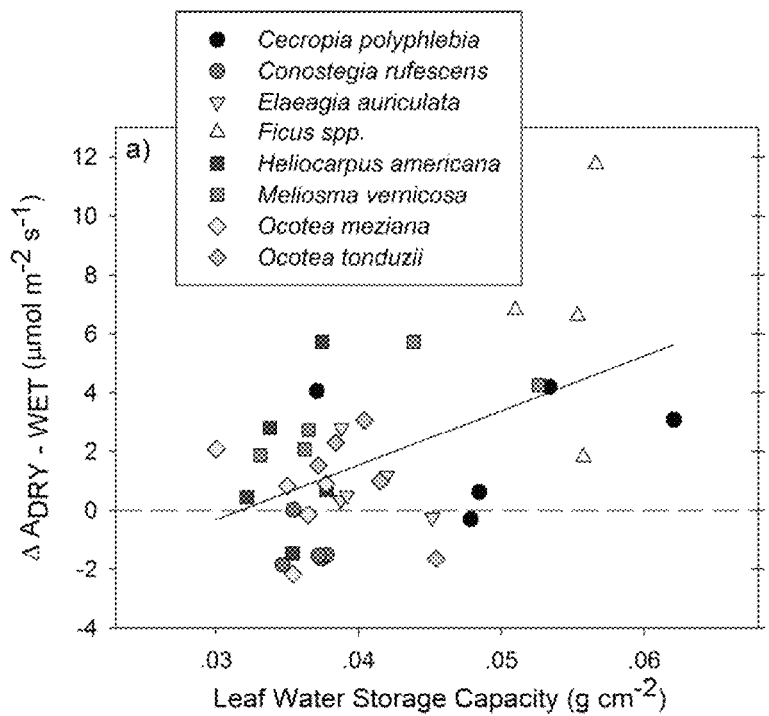
FIGS. 19A-B depict the difference in photosynthesis measured on dry versus wet leaves as a function of certain parameters.
Figure 19B:
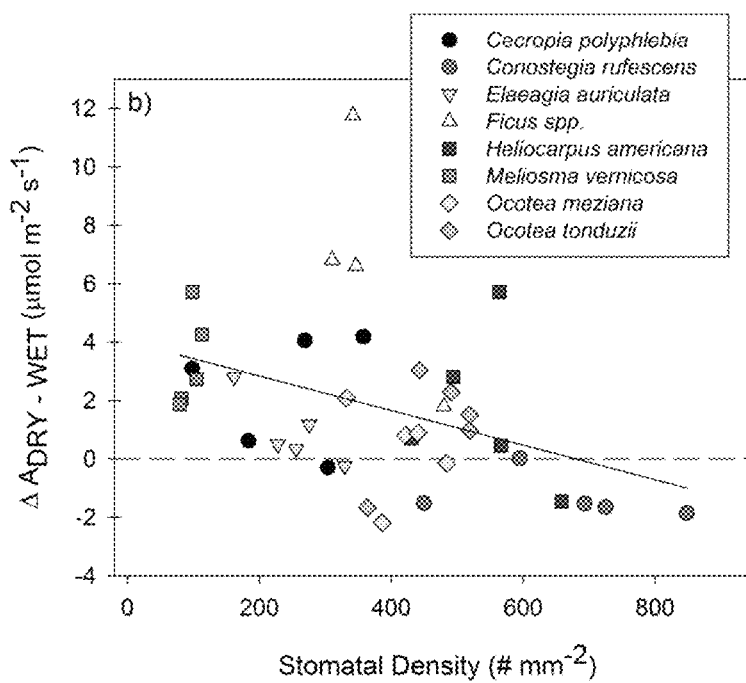

Whether leaf water storage capacity and stomatal density were related to $\Delta A_{DRY-WET}$ was then explored. $\Delta A_{DRY-WET}$ demonstrated a significant positive relationship with leaf water storage capacity ($F_{1,37}$=3.95, P=0.05, $r^2$=0.50; FIG. 19A) and a significant negative relationship with abaxial stomatal density ($F_{1,37}$=6.77, P=0.01, $r^2$=0.15; FIG. 19B). None of the species possessed adaxial stomata. Thus, leaves that retained more water per unit area and had fewer stomata had a greater positive difference between dry and wet $A_{net}$ values. Surprisingly, the presence of trichomes and leaf thickness did not explain the response of $A_{net}$ to leaf wetting.

TABLE 3

| Species | Leaf thickness (cm) | Specific leaf area (cm$^2$ g$^{-1}$) | Leaf dry matter content (mg g$^{-1}$) | Stomatal density (# mm$^{-2}$) | Stomatal length ($\mu$m) | Trichomes present (Yes/No) |
| --- | --- | --- | --- | --- | --- | --- |
| *Cecropia polyphlebia* | 0.309 ± 0.03 | 112.8 ± 13.6 | 230.1 ± 21.3 | 240 ± 27 | 7.93 ± 0.41 | Yes |
| *Conostegia rufescens* | 0.332 ± 0.03 | 130.0 ± 3.2 | 266.7 ± 6.2 | 662 ± 41 | 9.35 ± 0.28 | Yes |
| *Elaeagia auriculata* | 0.320 ± 0.01 | 101.6 ± 5.0 | 289.8 ± 12.3 | 250 ± 16 | 15.52 ± 0.30 | Yes |
| *Ficus* spp | 0.474 ± 0.09 | 65.2 ± 14.0 | 311.4 ± 62.9 | 345 ± 22 | 21.62 ± 1.18 | No |
| *Heliocarpus americana* | 0.255 ± 0.01 | 160.6 ± 10.7 | 237.1 ± 11.4 | 542 ± 25 | 12.23 ± 0.33 | No |
| *Meliosma vernicosa* | 0.244 ± 0.02 | 106.8 ± 16.8 | 286.6 ± 22.3 | 97 ± 4 | 20.76 ± 0.73 | Yes |
| *Ocotea meziana* | 0.251 ± 0.01 | 107.1 ± 8.9 | 328.7 ± 14.6 | 413 ± 16 | 17.09 ± 0.40 | No |
| *Ocotea tonduzii* | 0.333 ± 0.01 | 86.4 ± 7.4 | 349.5 ± 17.0 | 451 ± 18 | 12.20 ± 0.35 | No |

Photosynthesis of Wet and Dry Leaves

Photosynthesis was reduced for six of the species when leaves were wet as compared with when leaves were dry under direct light ($F_{6,28}$=3.49, P=0.011; FIG. 16A). Of the remaining species, photosynthesis was greater under wet conditions in *C. rufescens* and showed no change in *O. meziana*. The difference in dry and wet photosynthesis ($\Delta A_{DRY-WET}$) under diffuse light conditions was more consistent across species; all species except one had significantly higher $A_{net}$ under dry conditions (all P<0.025).

Figure 18A:
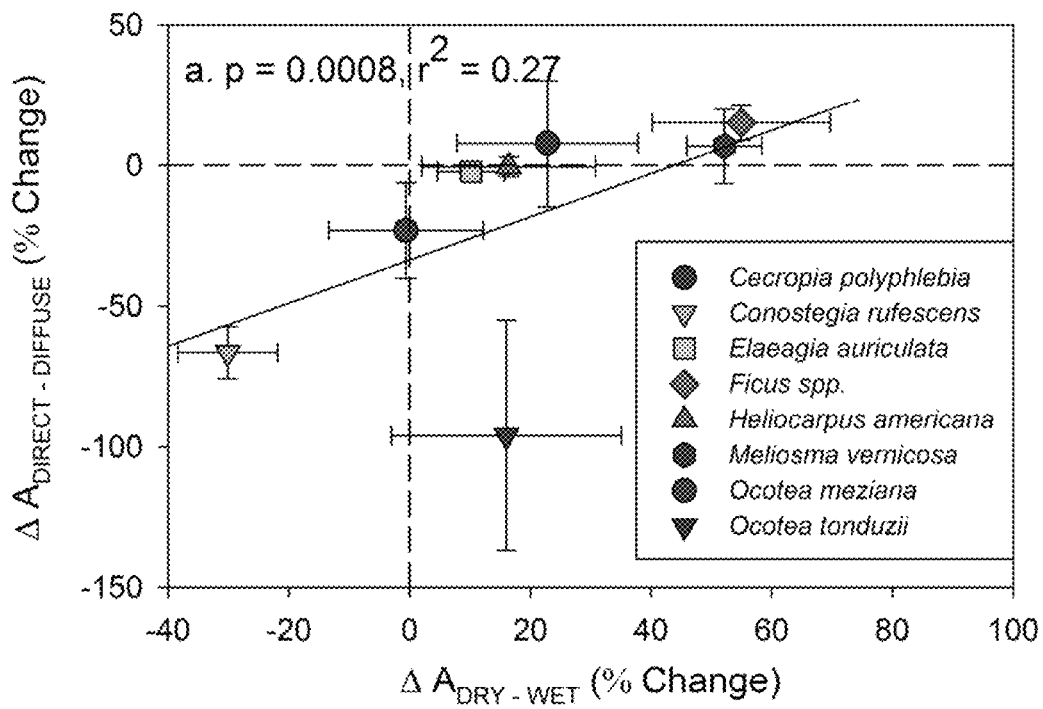
FIGS. 18A-C depict various relationships between the responses to diffuse light and certain parameters.
Figure 18B:
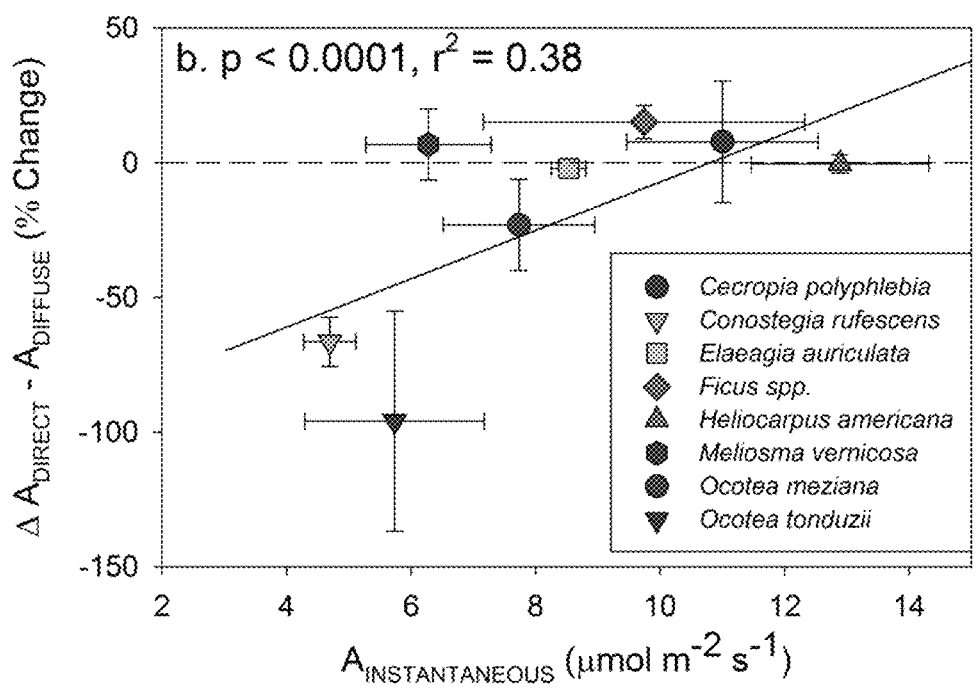
Figure 18C:
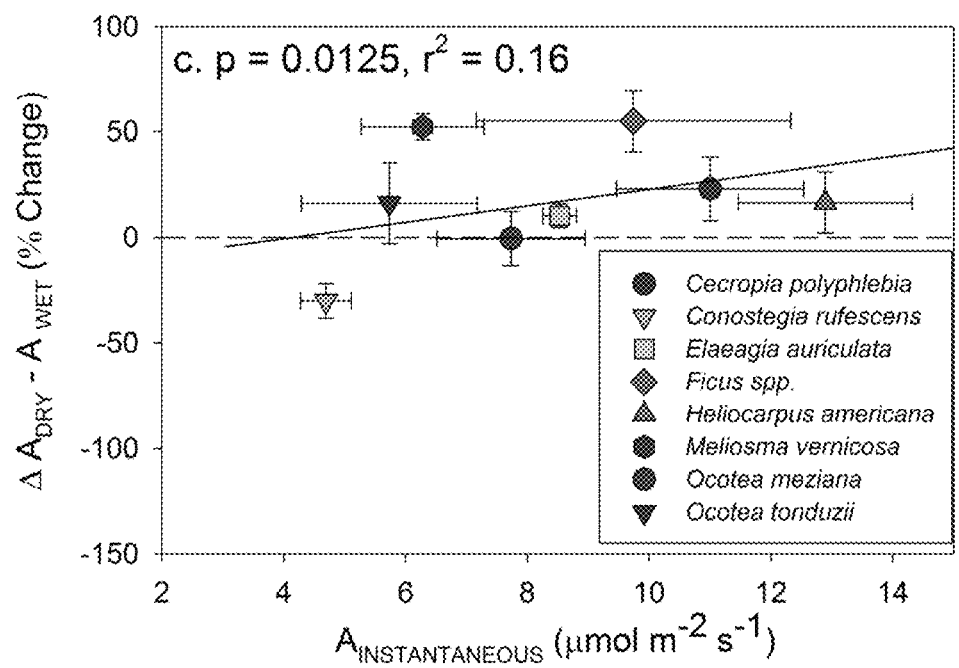
Figure 20:
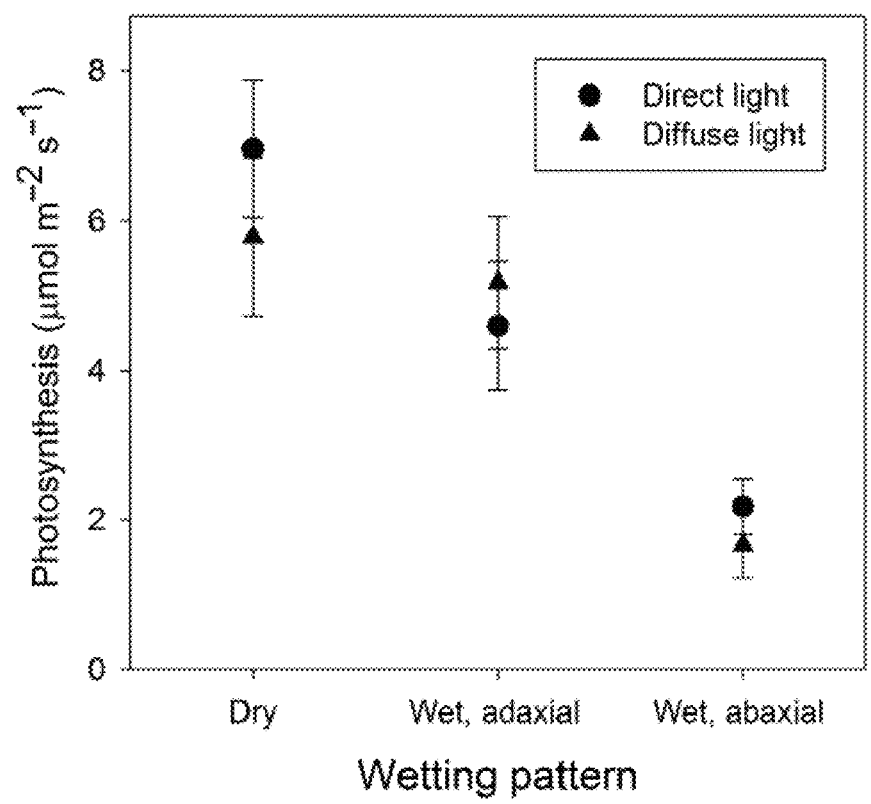
FIG. 20 depicts photosynthetic rates for subcanopy leaves of *Ocotea tonduzii* when dry, wet on the adaxial surface (top of leaf), and wet on the abaxial surface (bottom of leaf). Leaves were located 5-10 m off the ground under a closed canopy. Measurements were taken under both direct (circles) and diffuse (triangles) light conditions. Data are means of five individuals per treatment±SE.

Across all species, a significant positive relationship between $\Delta A_{DIRECT-DIFFUSE}$ and $\Delta A_{DRY-WET}$ was found ($F_{1,37}$=19.41, P<0.0001; FIG. 18A). Thus, species that had greater $A_{net}$ under diffuse light also had greater $A_{net}$ under wet conditions. There were also positive relationships between $A_{net}$ values under diffuse ($F_{1,37}$=18.56, P=0.0001; FIG. 18B) or wet ($F_{1,37}$=17.85, P=0.0002; FIG. 18C) conditions and $A_{net}$ values (instantaneous) under dry and direct To further explore the photosynthetic response to leaf wetting, photosynthetic rates for subcanopy leaves of *O. tonduzii* when leaves were dry, wet on the adaxial side, and wet on the abaxial side were compared (FIG. 20). Photosynthesis rates were 68-71% lower when the abaxial side of the leaf was wet compared with dry leaves ($F_{5,24}$=6.78, P=0.0005). In post hoc tests, there were no differences between diffuse and direct light photosynthesis within each treatment.

Comparing Photosynthesis in Common Environmental Conditions

Figure 21:
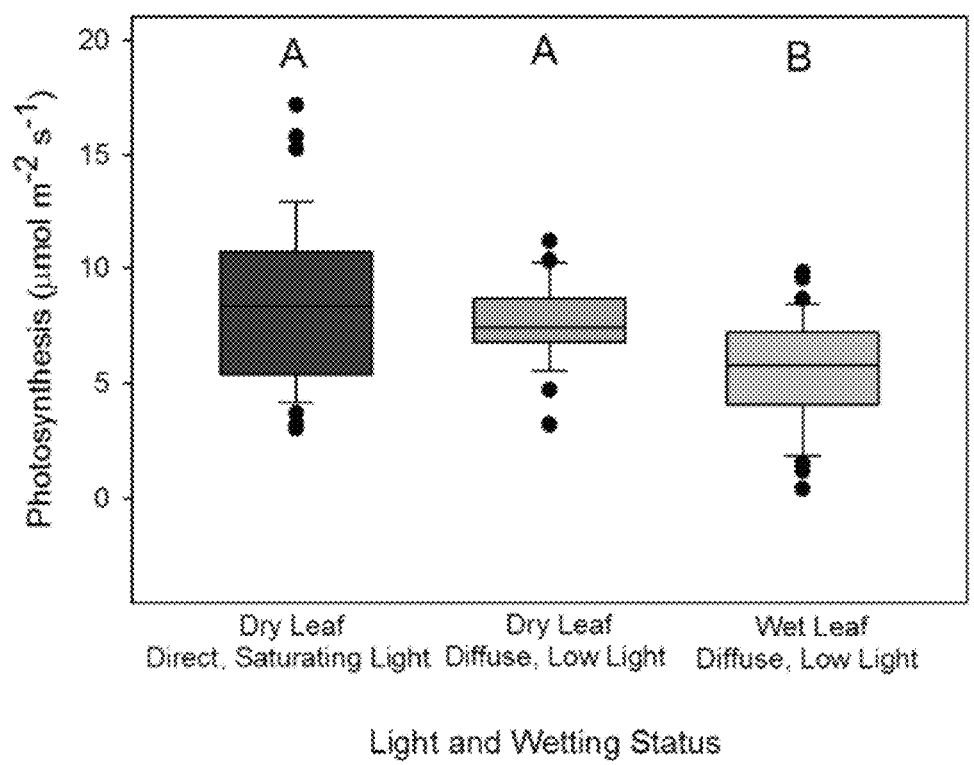
FIG. 21 depicts a boxplot of photosynthetic rates observed under three common environmental conditions: full sun (dry leaf, direct and saturating light); cloudy conditions (dry leaf, diffuse and low light); or rain or fog conditions (wet leaf, diffuse and low light). Boxplots represent the aggregate of eight different canopy tree species (n=5-7 per species). High-light or low-light values were calculated from light response curves and chosen as 1200 μmol m$^{-2}$ s$^{-1}$ (saturating light) or 400 μmol m$^{-2}$ s$^{-1}$ (low light). Significant differences were determined using Tukey's honestly significant difference and are denoted in the figure with (A) and (B) indicating significant differences.

Because clouds commonly reduce total available PAR, mean species' photosynthesis was compared for dry leaves given saturating direct light (1200 $\mu$mol m$^{-2}$ s$^{-1}$) with both wet and dry leaf diffuse light photosynthesis under low light (400 $\mu$mol m$^{-2}$ s$^{-1}$) (FIG. 21). The value of 400 $\mu$mol m$^{-2}$ s$^{-1}$ was used after analysis of local climate data, which found that fog typically reduces total solar radiation to 30-40% of maximum values. There were significant differences among the three scenarios, driven by significant reductions in photosynthesis under low diffuse light and wetting ($F_{2,116}$=12.06, P<0.001). The photosynthesis of wet leaves in low diffuse light was 33% (5.56 µmol m$^{-2}$ s$^{-1}$) lower than dry and saturating direct light conditions (8.49 µmol m$^{-2}$ s$^{-1}$). However, the mean rates of light-saturated photosynthesis under saturating direct light and diffuse, low light (7.61 µmol m$^{-2}$ s$^{-1}$) did not differ among species in post hoc comparisons.

Discussion

Figure 22:
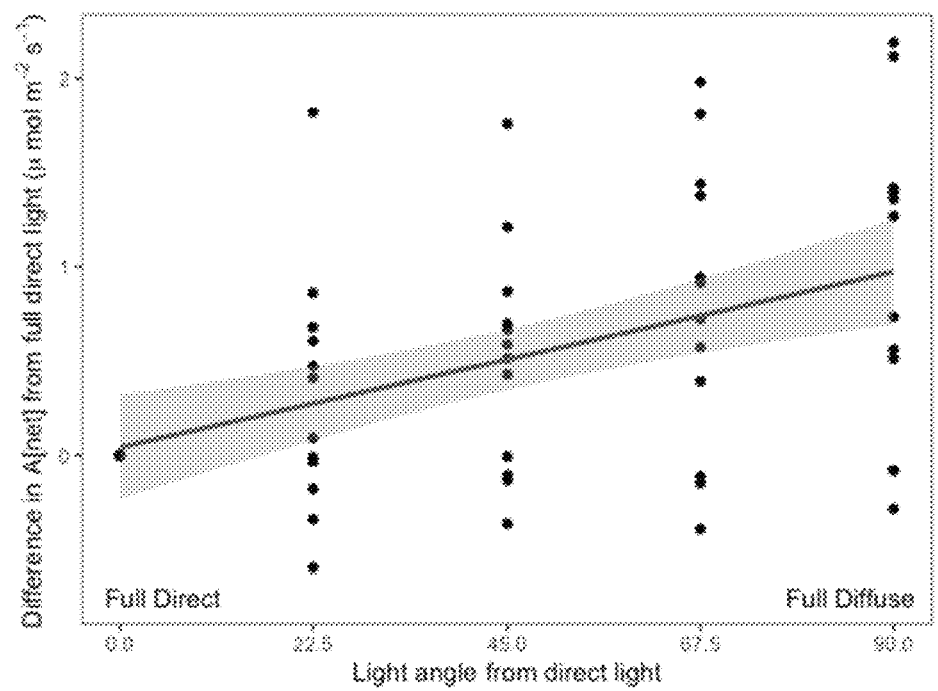
FIG. 22 depicts greater photosynthetic rates in diffuse light environments as compared to direct light environments for avocado trees (*Persea americana*).
Figure 23A:
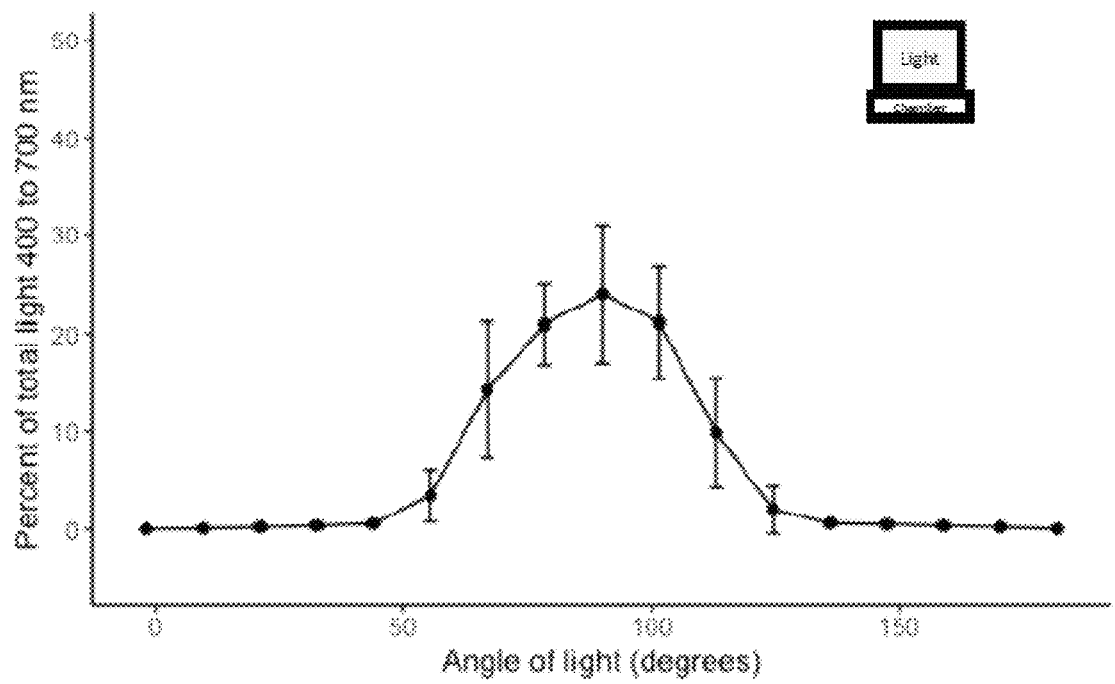
FIG. 23 depicts the percentage of light arriving at the leaf chamber as a function of the angle of that light. Data are shown with the light source directly on the leaf chamber, FIG. 23A, and at four different positions on the integrating sphere, FIG. 23B-E. The diagram in the corner of each figure is a visual representation of the experimental setup. Data represent means and one standard deviation.
Figure 23B:
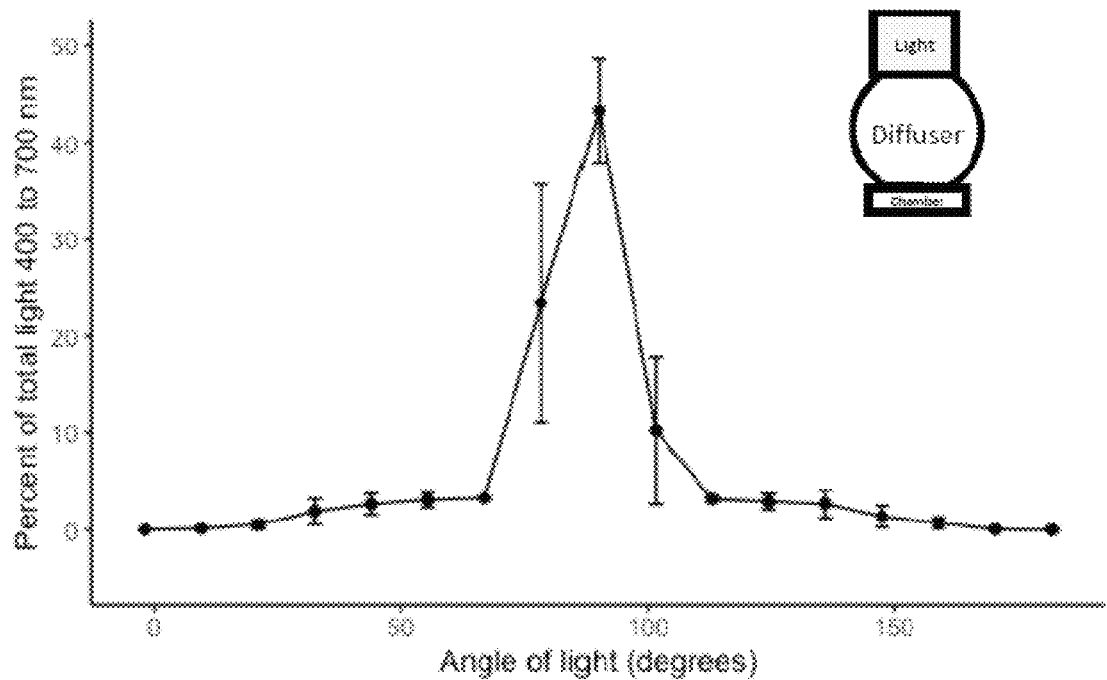
Figure 23C:
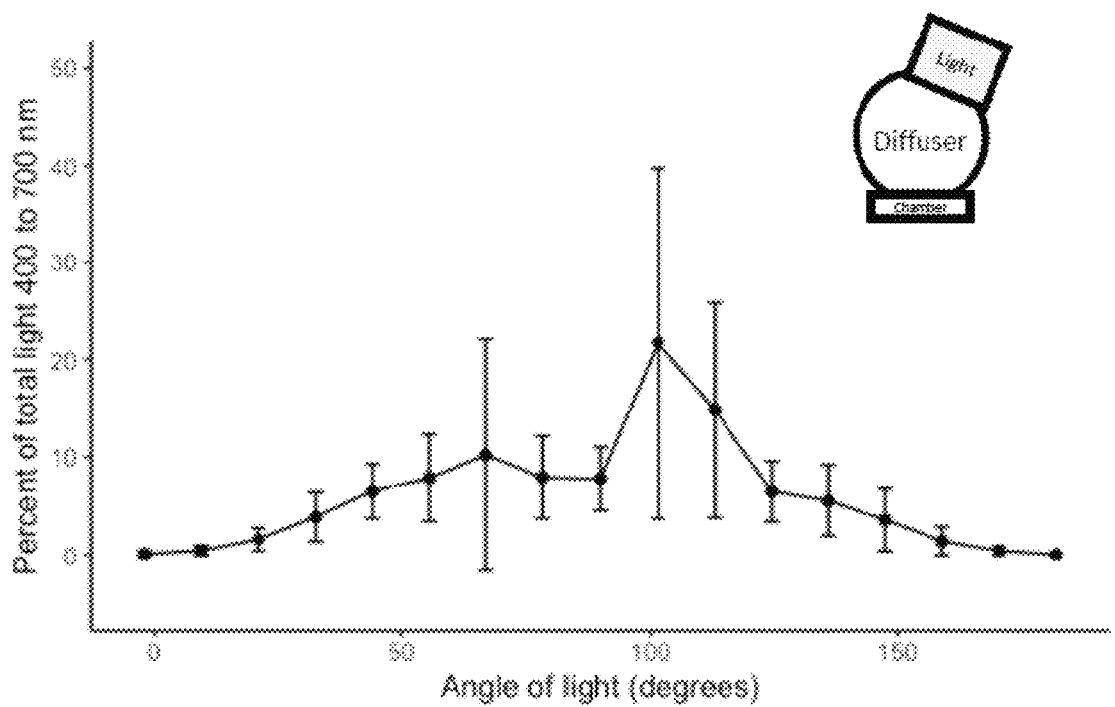
Figure 23D:
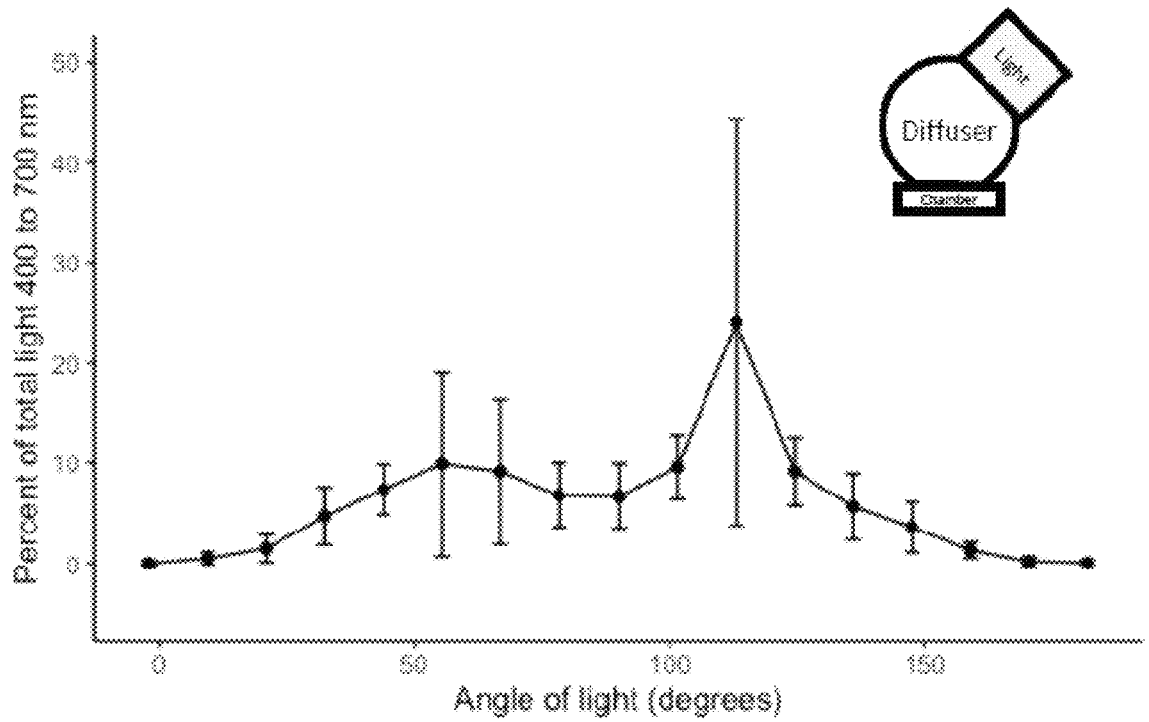
Figure 23E:
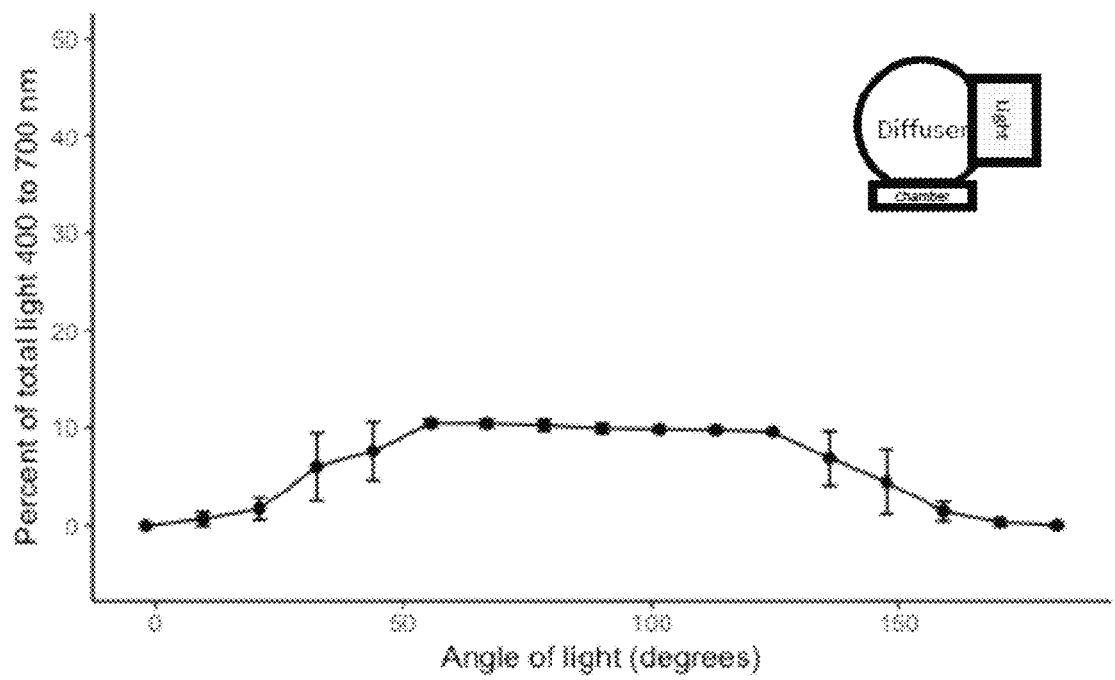

The results demonstrate species-specific differences in photosynthesis depending on the angle of light and wetness of leaves. Despite expectations that diffuse light would consistently reduce photosynthesis, species ranged from 100% greater photosynthetic rates under diffuse light conditions to 15% greater photosynthetic rates under direct light conditions at the same light intensity. Also demonstrated was that even when diffuse light environments have lower light intensities, photosynthesis is equal to that under direct light with high intensities, indicating greater light-use efficiency (FIG. 22). Leaf wetting primarily decreased photosynthesis, particularly when the leaf surface with stomata became wet. Interestingly, there was no consistent effect of species' successional status on the response to diffuse light or wetting (e.g. *C. rufescens*, *H. americanus*, and *C. polyphlebia* are considered canopy-emergent primary successional species). Ultimately, it was demonstrated that photosynthetic rates vary significantly across species in response to environmental conditions that are prevalent, yet are rarely considered in understanding net primary productivity of ecosystems. In the following, the mechanisms that might explain these differences are expanded on, and the implications for ecosystem primary productivity explored.

Photosynthesis Under Diffuse Light

The results indicate that some species have greater photosynthesis under diffuse light, while others have greater photosynthesis under direct light. Previous research has suggested that diffuse light results in higher absorption of light in the upper palisade layer, resulting in less light penetrating deeper into leaves and leading to a 10-15% reduction in the photosynthetic rates of two herbaceous species. These studies also propose that sun-grown leaves have greater direct light photosynthesis relative to diffuse light as a result of a thicker palisade mesophyll (and greater overall thickness) which facilitates light penetration deeper into the leaf. Limited light penetration may be true in some species, but the results suggest that this is not universal. While all leaves were sun-exposed, species with greater photosynthesis under diffuse light were thicker, a characteristic of sun leaves, but also had low light saturation points, a characteristic of shade leaves (FIGS. 17C-D). This suggests that photosynthesis under diffuse conditions is driven by more than just leaf thickness. Leaf biochemistry could explain these responses. Enhanced diffuse light photosynthesis could be driven by greater chloroplast concentration in the upper layers of palisade mesophyll cells or by improved efficiency through greater electron transport rates (J max), the maximum rates of carboxylation (V cmax), or the quantum yield of photosystem II (PPSII). Understanding the mechanisms driving differences in photosynthesis in diffuse light adds to the ability to predict the response of primary productivity to changing cloud cover conditions.

Figure 12:
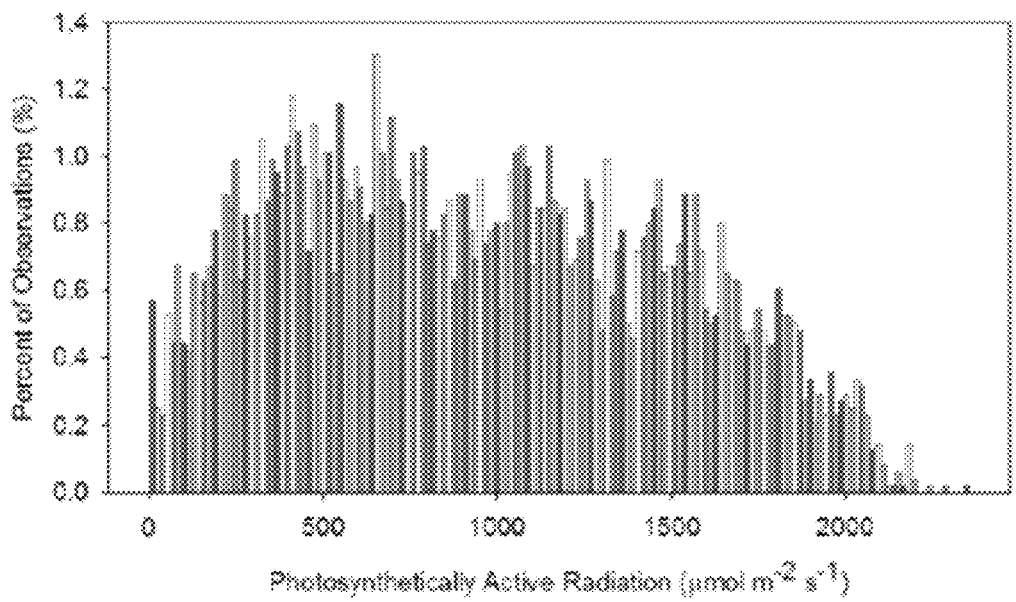
FIG. 12 depicts distribution of midday hours (1200 to 1400 solar time) spent at different levels of photosynthetically active radiation (PAR). Data were collected every 15 minutes from a tower above the canopy in Monteverde, Costa Rica. Hourly averages were then sorted into each range of PAR and percentage calculated as the number of hours at that PAR level over the total number of hourly observations. Each bar represents a range of 15 µmol $m^{-2}s^{-1}$.

In natural conditions, diffuse light is often accompanied by changes to light intensity. Diffuse light is the result of scattering as a result of aerosols and clouds, which typically results in less total light arriving at the canopy. But this reduction in light intensity may not lead to reduced photosynthesis. In the study site, midday light intensities are >400 µmol m$^{-2}$ s$^{-1}$ for 81% of the time, meaning that all study species spend the majority of the time above their light saturation point (FIG. 12). The average response across species demonstrates that the increase in diffuse light photosynthesis can compensate for reduced light intensity, ultimately increasing the light-use efficiency of forest canopies (FIG. 21). The improved light-use efficiency of leaves of certain species in diffuse light adds an additional explanation to studies that demonstrate greater ecosystem productivity under these conditions.

The spectral quality of light also changes in diffuse conditions with increased percentage of blue wavelengths and red:far-red ratios. These spectral changes are known to increase stomatal aperture and total photosynthetic rate and lead to greater canopy productivity. While this study did not test spectral quality (direct and diffuse light had similar spectra), these potential changes only further increase photosynthesis under diffuse light. Thus, the reduction in diffuse light photosynthesis for some species in this study may be compensated for by increased stomatal conductance. The total photosynthetic rate of a canopy is dependent on species-level responses to directionality, intensity and spectral quality, with the net effect largely increasing photosynthesis in diffuse light.

Photosynthesis During Leaf Wetting

Wetting of the adaxial surface of the leaf resulted in reduced photosynthetic rates in six of eight species. A similar study found reductions in photosynthesis in nine out of 10 species from a temperate savanna and tropical rainforest. However, both studies demonstrate notable variation across species. The proposed mechanism of water creating a $CO_2$ diffusion barrier misses a key point; in many tree species (and this study) wetting mostly occurs on the adaxial side of a horizontally oriented leaf, while most species have stomata predominantly on abaxial sides of leaves. Leaf wetting should also change the water status of the leaf through foliar water uptake, create a more humid boundary layer on the bottom of the leaf, and scatter light. However, all of these effects increase stomatal conductance and photosynthesis, which explains the increased photosynthesis during wetting in *C. rufescens*. It is possible that *C. rufescens* has greater stomatal conductance or foliar water uptake under wet conditions, driving the increased photosynthesis. But for species with reduced photosynthesis in wet conditions, there is a lack of a clear mechanism. Despite this, it was found that species capable of storing greater quantities of water on their leaf surfaces and those that have fewer stomata show the greatest reductions in photosynthesis when wet (see FIGS. 19A-B). While these relationships cannot resolve the mechanism(s), they suggest that traits that confer water retention and C uptake are linked to photosynthesis under wet conditions.

The results of this study demonstrate at least three different ways to maximize photosynthesis given wet conditions. The first, which has long been presumed to be the most common, is that species in wet ecosystems need to avoid being wet for extended periods; that is, these species have leaf surface properties (cuticle structures or waxy layers) that make them very hydrophobic. However, another study demonstrated that tropical rainforest leaves are largely hydrophilic, so many species must be able to maximize photosynthesis despite having leaves where water spreads across the surface. Second, species can have suites of leaf traits that maximize daily C gain through higher photosynthetic rates during dry conditions, thus compensating for low photosynthesis during wet conditions. Finally, other species may have stomata on abaxial surfaces where wetting is less likely to occur, thus minimizing the inhibition of photosynthesis during wetting events. With recent estimates demonstrating that tropical rainforest canopies experience wetting on more than half the days of the year, it is logical that multiple functional strategies have evolved to maximize photosynthesis.

Ecosystem Implications

Changes in light intensity, light quality and leaf wetting often occur in tandem, such as when clouds bring rainfall and diffuse light simultaneously. It was found that when leaves are wet, photosynthetic rates are greater or equal under diffuse vs direct light conditions (FIG. 16B). The fact that species with greater direct light photosynthesis had lower values under wet conditions while those with greater diffuse light photosynthesis were relatively unaffected reinforces a critical point: that the response to diffuse light and wet conditions varied similarly across species. In other words, species with greater photosynthesis under diffuse light tended to have greater photosynthesis in wet conditions. It is possible that the structural and functional traits that maximize photosynthesis in diffuse light might also serve similar functions for leaf wetness. Additionally, it is likely that films of water on leaf surfaces cause some additional scattering functionally, resulting in diffuse conditions even if incoming light is predominantly direct.

These results provide an additional explanation for ecosystem studies demonstrating that diffuse light conditions can increase the light-use efficiency and total C stored. This diffuse fertilization effect posits that diffuse light can penetrate deeper into complex canopies and illuminate many understory leaves. The results find that increased ecosystem diffuse light photosynthesis can also be explained by a species assemblage that has increased leaf photosynthesis in diffuse light. Ecosystem photosynthesis of wet canopies is less clear, as standard methods (e.g. eddy covariance) do not work in wet conditions, and disentangling the effects of canopy wetting from diffuse light remains challenging.

Anthropogenic climate change will alter cloud cover, influencing light intensity and quality as well as the frequency and duration of leaf wetting. While understanding how cloud patterns will change given future climate scenarios remains difficult, ensemble models such as CMIP5 project major changes to precipitation variability (e.g. dry sunny days vs cloudy and rainy days) in the future. At tropical latitudes, models project an increase in cloud cover and higher cloud bases, which may lead to increased diffuse light periods. Additionally, another study modeled an increase in the diffuse radiation fraction during a 39 year period, leading to a 23.7% increase in the net ecosystem exchange. Similar research on the ecosystem effects of leaf wetting on productivity remains limited. Linking the integrated effects of changing cloud patterns to empirical data on changes in ecosystem productivity will be a key feature to improving models.

Conclusions

Almost every measurement of leaf-level photosynthesis is made on a dry leaf experiencing direct light. However, this is a vast oversimplification of the complex environmental conditions experienced by most plants. It is easy to assume that diffuse light and leaf wetting are conditions under which minimal photosynthesis is expected and therefore only nominal contributions to ecosystem primary productivity. However, the results indicate that photosynthesis does not cease under these conditions. In fact, certain species can double their photosynthetic rates under diffuse light conditions. Even at lower light intensities, diffuse light photosynthesis can still be equal to or greater than direct light photosynthesis at saturating light intensities. This could help to explain the growing number of studies that demonstrate higher net ecosystem exchange when it is cloudy. Rather, the single most detrimental effect on photosynthesis is likely to be when canopies are wet. However, this is not driven by $CO_2$ limitation, as reductions still occur despite wetting only in areas without stomata. Importantly, the directionality and magnitude of these changes are likely to be highly species-specific. Ultimately, understanding the effects of light quality and leaf wetting on photosynthesis, as well as how this varies among plant functional types, allows for better constrain estimates of primary productivity in Earth systems models.

Example 2. Effects of Differing Proportions of Diffuse Light on Photosynthesis in Avocado In this experiment, the relationship between plant photosynthesis (described as: A[net]) and the proportion of diffuse light that arrives at the leaf (described as the angle of offset from full diffuse light) was determined. This was performed by utilizing a light diffusing sphere described herein interfaced with the LI-COR LI-6800 portable infrared gas analyzer to collect leaf photosynthesis data at five positions along the track that represent a range of light qualities from full direct light to full diffuse light. Photosynthesis was measured on mature leaves of 12 avocado trees (*Persea americana*). FIG. 22 demonstrates that a change in light quality leads to a significant relationship between these two variables, whereby photosynthetic rates are greater in diffuse light environments as compared to direct light environments.

Example 3

Methods-Setup

To assess the angular distribution of light sources used with different portable infrared gas analyzers used for plant gas exchange, the amount of light reaching a fiber optic cable mounted at different angles (horizontal to vertical) below the light source was measured. The fiber optic cable was mounted to a rotational stage that allowed for it to be tilted at precise angles across a 180° field of view. The cable had a 105 µm core diameter, a 0.1 numerical aperture, such that the angle of acceptance was 11.5° (M96L02; ThorLabs, Inc., Newton, New Jersey). The fiber optic cable was mounted just below the top of the leaf chamber in the position where a leaf would typically be located. The fiber optic was then rotated at 11.5° increments across the field of view (horizontal-vertical-horizontal) to collect spectra at 17 discrete angles. The fiber optic cable was connected to a CCS100 compact spectrometer (350-700 nm; ThorLabs, Inc., Newton, New Jersey).

Spectra were Collected with and without the Integrating Sphere

The angular distribution of light was quantified for five distinct experimental setups: (1) a control with the light source directly on top of the leaf chamber, (2) the light source at 90° directly on top of an integrating sphere described herein (i.e, light presumably emanating perpendicular to the leaf surface), (3) the light source at a 67.5° on an integrating sphere described herein, (4) the light source at a 45° on an integrating sphere described herein, and (5) the light source at a 0° on the side of an integrating sphere described herein (i.e, light presumably emanating parallel to the leaf surface). For each setup, spectra were collected across the field of view at random positions within the leaf chamber (n=10 to 25 positions per experimental setup). Because the rotational stage only moves along one axis, spectra in two cardinal directions was collected (i.e., front-to-back and left-to-right). Light quantity was held constant at 1390 µmol m$^{-2}$ s$^{-1}$ and the distribution of wavelengths was held constant using the same proportions of LEDs in the light source (65% red, 20% blue, 10% green, 5% white). Measurements were made with the small (6800-02) and large (6800-03) light sources from the LI-6800 (LI-COR Biosciences, Lincoln, Nebraska) and the small light source (6400-02B) from the LI-6400XT (LI-COR Biosciences, Lincoln, Nebraska). Only results from the LI-6800 with the large light source connected to the large chamber (36 cm$^2$ area) and the integrating sphere are shown here.

Data Processing

To determine the total quantity of light for each spectra, the area under the curve from 400-700 nm was integrated, the wavelengths commonly referred to as photosynthetically active radiation (PAR). This was performed utilizing numerical integration using the trapezoidal rule where a series of trapezoidal areas are created under the curve and then summed to determine the total area (SciPy, 2020). A trapezoid was computed between each data point resulting in 3647 distinct trapezoids for our data set. The numerical integration was computed using a Python script and processed in JupyterLab v2.2.6 (Project Jupyter, Worldwide). The total integrated area was summed from each of the 17 distinct curves created for each replicate. The percent of light arriving at each angle was determined as the amount of light at that angle divided by the total. The 10 to 25 replicates for each experimental setup were averaged to create FIGS. 23a-e. All figures were made in R Studio v1.4.110 (R Studio, Boston, USA) using R v4.0.3 (R Foundation for Statistical Computing, Vienna, Austria).

Results

The integrating sphere described herein alters the distribution of light from the LI-6800 light source by both making light more direct when mounted directly on top of the sphere (90°) and diffuse when the light is mounted on the side of the sphere)(0° (FIGS. 23a-e). One way to assess the diffuseness of light is to quantify the percentage of light arriving as predominantly direct, defined here as light arriving at 90±5.75° and arriving at 90±17.25° (Table 4). For the control (no integrating sphere), the percent of light arriving at 90±5.75° and arriving at 90±17.25° was 23.9±7.0 and 65.9±9.9, respectively. With the light mounted directly on top of the sphere, these percentages increased to 43.3±5.4 and 77.0±15.4, respectively. Conversely, when the light is mounted on the side of the sphere (0°), these percentages are reduced to only 9.9±0.5 and 29.9±0.8, respectively. The intermediate positions on the sphere provide intermediate percentages of predominantly direct light, allowing the user to manipulate the amount of diffuse light reaching the leaf surface by rotating the light source around the outside of the integrating sphere.

Table 4 depicts the percentage of light arriving at the leaf chamber as predominantly direct light (90°-perpendicular to leaf surface). Data are shown as the percentage of light arriving at 90±5.75° and arriving at 90±17.25°. Data represent means and one standard deviation.

TABLE 4

| Light Setup | Percent Arriving at 90 ± 5.75° | Percent Arriving at 90 ± 17.25° |
| --- | --- | --- |
| Control | 23.9 ± 7.0 | 65.9 ± 9.9 |
| Sphere 90° | 43.3 ± 5.4 | 77.0 ± 15.4 |
| Sphere 67.5° | 7.8 ± 3.2 | 37.4 ± 18.8 |
| Sphere 45° | 6.7 ± 3.2 | 23.0 ± 5.5 |
| Sphere 0° | 9.9 ± 0.5 | 29.9 ± 0.8 |

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A light diffuser device comprising:
    a sphere having at least two openings, wherein one opening includes a track and the other opening includes a base having supports;
    one or more plates positioned on the track; and
    a cart including a light source positioned on the track.

2. The light diffuser device of claim 1, wherein the base having supports is configured to attach to a gas analyzer.

3. The light diffuser device of claim 1, wherein the base having supports is secured to the sphere via a fastener.

4. The light diffuser device of claim 2, wherein the base having supports slides onto a leaf chamber of the gas analyzer.

5. The light diffuser device of claim 2, wherein the gas analyzer is an infrared, portable gas analyzer.

6. The light diffuser device of claim 1, wherein the cart including the light source is positioned at an angle.

7. The light diffuser device of claim 1, wherein the cart including the light source is secured to the track via a fastening mechanism.

8. The light diffuser device of claim 6, wherein the angle is 67.5°.

9. The light diffuser device of claim 6, wherein the angle is 90°.

10. The light diffuser device of claim 6, wherein the angle is 0°.

11. The light diffuser device of claim 6, wherein the angle is denoted by a combination of tick marks and numbers.

12. The light diffuser device of claim 11, wherein the combination of tick marks and numbers are located on an outer portion of one side of the track.

13. The light diffuser device of claim 1, wherein the track is rectangular and runs 120 degrees around the side of the sphere.

14. The light diffuser device of claim 1, wherein the light source is a light-emitting diode.

15. The light diffuser device of claim 1, wherein the one or more plates are positioned on the track to close the sphere.

16. A method of using a light diffuser device comprising:
    a sphere having at least two openings, wherein one opening includes a track and the other opening includes a base having supports;
    positioning a cart including a light source on the track at a desired angle;
    securing the cart including the light source to the track via a securing mechanism;
    sealing exposed locations of the track with one or more plates;
    positioning the base having supports onto a leaf chamber of a gas analyzer.

17. The method of claim 16, further comprising setting the light source at a desired intensity and spectra.

18. The method of claim 17, wherein a leaf in the leaf chamber of the gas analyzer equilibrates the conditions and a leaf gas exchange is measured using the gas analyzer.

19. The method of claim 16, wherein the securing mechanism occurs via a fastener.

20. The method of claim 16, wherein the base having supports is secured to the sphere via a fastener.

* * * * *